United States Patent
Sperandio et al.

(10) Patent No.: US 12,254,623 B2
(45) Date of Patent: Mar. 18, 2025

(54) ARTIFICIAL INTELLIGENCE ASSISTED DIAGNOSIS AND CLASSIFICATION OF LIVER CANCER FROM IMAGE DATA

(71) Applicant: GE Precision Healthcare LLC, Milwaukee, WI (US)

(72) Inventors: Mélodie Sperandio, Paris (FR); Lorraine Jammes, Montrouge (FR); Marine Loth, Noisy-le-Roi (FR); Baptiste Perrin, Buc (FR); Mireille Haddad, Villejuif (FR); Véronique Claire Jacqueline Ferry, Villeurbanne (FR)

(73) Assignee: GE Precision Healthcare LLC, Waukesha, WI (US)

( * ) Notice: Subject to any disclaimer, the term of this patent is extended or adjusted under 35 U.S.C. 154(b) by 571 days.

(21) Appl. No.: 17/366,778

(22) Filed: Jul. 2, 2021

(65) Prior Publication Data

US 2022/0318991 A1    Oct. 6, 2022

Related U.S. Application Data

(60) Provisional application No. 63/169,665, filed on Apr. 1, 2021.

(51) Int. Cl.
    *G06T 7/00*      (2017.01)
    *G16H 30/40*   (2018.01)
    *G16H 50/20*   (2018.01)

(52) U.S. Cl.
    CPC ........... *G06T 7/0012* (2013.01); *G16H 30/40* (2018.01); *G16H 50/20* (2018.01);
    (Continued)

(58) Field of Classification Search
    CPC ............... G06T 2200/24; G06T 7/0012; G06T 2207/30096; G06T 2207/20081;
    (Continued)

(56) References Cited

U.S. PATENT DOCUMENTS

| 9,092,691 B1 | 7/2015 | Beaumont et al. |
| 10,373,314 B2 | 8/2019 | Gillies et al. |
| (Continued) | | |

FOREIGN PATENT DOCUMENTS

| WO | WO-2012040410 A2 * | 3/2012 | ........... G06T 7/0016 |
| WO | WO-2016004330 A1 * | 1/2016 | ........ G06F 17/30247 |

OTHER PUBLICATIONS

Seung Soo Kim, Li-RADS v2017 categorisation of HCC using CT: Does moderate to severe fatty liver affect accuracy?, 2019, Issue 29, European Radiology, pp. 186-194 (Year: 2019).*

(Continued)

*Primary Examiner* — Vu Le
*Assistant Examiner* — Lei Zhao
(74) *Attorney, Agent, or Firm* — Amin, Turocy & Watson, LLP

(57) ABSTRACT

Techniques are described for computer-aided diagnostic evaluation of liver exams. A method embodiment comprises rendering, by a system operatively coupled to a processor, medical images of a liver of a patient in a graphical user interface (GUI) of a medical imaging application that facilitates evaluating liver imaging exams. The method further comprises identifying, by the system, an observation on the liver as depicted in one or more of the medical images and evaluating defined imaging features associated with the observation as depicted in the one or more medical images. The method further comprises providing, by the system, feature information regarding the defined imaging features via the GUI.

21 Claims, 14 Drawing Sheets

(52) U.S. Cl.
CPC ............... G06T 2200/24 (2013.01); G06T 2207/30056 (2013.01); G06T 2207/30096 (2013.01)

(58) Field of Classification Search
CPC ........... G06T 2207/20084; G06T 2207/30056; G16H 30/40; G16H 50/20
See application file for complete search history.

(56) References Cited

U.S. PATENT DOCUMENTS

| | | |
|---|---|---|
| 2005/0232474 A1 | 10/2005 | Wei et al. |
| 2006/0064396 A1* | 3/2006 | Wei ..................... A61B 6/463 |
| 2013/0129168 A1 | 5/2013 | Ross |
| 2016/0174895 A1 | 6/2016 | Ross et al. |
| 2020/0085382 A1 | 3/2020 | Taerum et al. |

OTHER PUBLICATIONS

Granata et al., Major and ancillary features according to LI-RADS in the assessment of combined hepatocellular-cholangiocarcinoma, Radiology and Oncology, Jun. 2020; 54(2): 149-158.*

Mohamed et al., Detection of CT-Liver Lesions using Otsu Algorithm and Morphological Operations, 2019 International Conference on Computer, Control, Electrical, and Electronics Engineering (ICCCEEE), Sep. 21-23, 2019).*

Corwin et al., "Differences in Liver Imaging and Reporting Data System Categorization Between MRI and CT", AJR Am J Roentgenol, vol. 206, Feb. 2016, pp. 307-312.

Ehman et al., "Rate of observation and inter-observer agreement for LI-RADS major features at CT and MRI in 184 pathology proven hepatocellular carcinomas", Abdominal Radiology, vol. 41, Jan. 2, 2016, pp. 963-969.

Zhang et al., "Liver Imaging Reporting and Data System:: Substantial Discordance Between CT and MR for Imaging Classification of Hepatic Nodules", Academic Radiology, vol. 23, No. 3, Mar. 2016, pp. 344-352.

Basha et al., "Diagnostic efficacy of the Liver Imaging-Reporting and Data System (LI-RADS) with CT imaging in categorising small nodules (10-20 mm) detected in the cirrhotic liver at screening ultrasound", Clinical Radiology, vol. 72, 2017, 11 pages.

Cha et al., "Liver Imaging Reporting and Data System on CT and gadoxetic acid-enhanced MRI with diffusion-weighted imaging", Eur Radiol, vol. 27, 2017, pp. 4394-4405.

Joo et al., "Liver imaging reporting and data system v2014 categorization of hepatocellular carcinoma on gadoxetic acid-enhanced MRI: Comparison with multiphasic multidetector computed tomography", J Magn Reson Imaging, vol. 45, 2017, pp. 731-740.

Kim et al., "Diagnostic Performance of Gadoxetic Acid-enhanced Liver MR Imaging versus Multidetector CT in the Detection of Dysplastic Nodules and Early Hepatocellular Carcinoma", Radiology, vol. 285, 2017, 13 pages.

Chernyak et al., "Liver Imaging Reporting and Data System: Discordance Between Computed Tomography and Gadoxetate-Enhanced Magnetic Resonance Imaging for Detection of Hepatocellular Carcinoma Major Features", J Comput Assist Tomogr, vol. 42, No. 1, 2018, pp. 155-161.

Corwin et al., "Nonstandardized Terminology to Describe Focal Liver Lesions in Patients at Risk for Hepatocellular Carcinoma: Implications Regarding Clinical Communication", AJR Am J Roentgenol, vol. 210, 2018, pp. 85-90.

Fraum et al., "Differentiation of Hepatocellular Carcinoma from Other Hepatic Malignancies in Patients at Risk: Diagnostic Performance of the Liver Imaging Reporting and Data System Version 2014", Radiology, vol. 286, 2018, pp. 158-172.

Alhasan et al., "LI-RADS for CT diagnosis of hepatocellular carcinoma: performance of major and ancillary features", Abdom Radiol, vol. 44, 2019, pp. 517-528.

An et al., "Intraindividual Comparison between Gadoxetate-Enhanced Magnetic Resonance Imaging and Dynamic Computed Tomography for Characterizing Focal Hepatic Lesions: A Multicenter, Multireader Study", Korean J Radiol, vol. 20, 2019, pp. 1616-1626.

Chan et al., "Diagnostic imaging of hepatocellular carcinoma at community hospitals and their tertiary referral center In the era of LI-RADS: a quality assessment study", Abdominal Radiology, vol. 44, 2019, pp. 4028-4036.

Kim et al., "LI-RADS v2017 categorisation of HCC using CT: Does moderate to severe fatty liver affect accuracy?", European Radiology, vol. 29, 2019, pp. 186-194.

Nakao et al., "Liver imaging reporting and data system (LI-RADS) v2018: comparison between computed tomography and gadoxetic acid-enhanced magnetic resonance imaging", Japanese Journal of Radiology, vol. 37, 2019, pp. 651-659.

Ominde et al., "Multicentre study on dynamic contrast computed tomography findings of focal liver lesions with clinical and histological correlation", SA Journal Radiology, vol. 23, 2019, 7 pages.

Seo et al., "Optimal criteria for hepatocellular carcinoma diagnosis using CT in patients undergoing liver transplantation", European Radiology, vol. 29, 2019, pp. 1022-1031.

Yoon et al., "Added Value of sequentially performed gadoxetic acid-enhanced liver MRI for the diagnosis of small (10-19 mm) or atypical hepatic observations at contrast-enhanced Ct: A prospective comparison", J Magn Reson Imaging, vol. 49, 2019, pp. 574-587.

Alenazi et al., "Clinicians and surgeon survey regarding current and future versions of CT/MRI LI-RADS", Abdominal Radiology, vol. 45, 2020, pp. 2603-2611.

Barabino et al., "LI-RADS to categorize liver nodules in patients at risk of HCC: tool or a gadget in daily practice?", Radiologia Medica, vol. 126, 2021, pp. 5-13.

Lee et al., "CT and MRI Liver Imaging Reporting and Data System Version 2018 for Hepatocellular Carcinoma: A Systematic Review With Meta-Analysis", Journal of the American College of Radiology, vol. 17, No. 10, Oct. 2020, pp. 1199-1206.

Min et al., "Magnetic Resonance Imaging With Extracellular Contrast Detects Hepatocellular Carcinoma With Greater Accuracy Than With Gadoxetic Acid or Computed Tomography", Clinical Gastroenterology and Hepatology, vol. 18, No. 9, 2020, 17 pages.

Ren et al., "The role of ancillary features for diagnosing hepatocellular carcinoma on CT: based on the Liver Imaging Reporting and Data System version 2017 algorithm", Clinical Radiology, vol. 75, Jun. 2020, 11 pages.

Yamashita et al., "Deep convolutional neural network applied to the liver imaging reporting and data system (LI-RADS) version 2014 category classification: a pilot study", Abdominal Radiology, vol. 45, 2020, pp. 24-35.

Cho et al., "Diagnostic Performance of Liver Imaging Reporting and Data System in Patients at Risk of both Hepatocellular Carcinoma and Metastasis", Abdominal Radiology, vol. 45, 2020, pp. 3789-3799.

Cunha et al., "Imaging Diagnosis Of Hepatocellular Carcinoma: LI-RADS", Chinese Clinical Oncology, vol. 10. No. 1, May 14, 2021, 11 pages.

Pizzi et al., "Multimodality Imaging of Hepatocellular Carcinoma: From Diagnosis to Treatment Response Assessment in Everyday Clinical Practice", Canadian Association of Radiologists Journal, 2020, 14 pages.

Ding et al., "Contrast-Enhanced Ultrasound LI-RADS 2017: Comparison with CT/MRI LI-RADS", European Radiology, 2020, 8 pages.

Fraum et al., "Assessment of Primary Liver Carcinomas Other than Hepatocellular Carcinoma (HCC) with LI-RADS V2018: Comparison of the LI-RADS Target Population to Patients Without LI-RADS-Defined HCC Risk Factors", European Radiology, vol. 30, 2020, pp. 996-1007.

Granata et al., "Major and Ancillary Features According to LI-RADS in the Assessment of Combined Hepatocellular-Cholangiocarcinoma", Radiology and Oncology, 2020, pp. 149-158.

(56) References Cited

OTHER PUBLICATIONS

Huang et al., "Diagnostic Accuracy of CEUS LI-RADS for the Characterization of Liver Nodules 20 mm or Smaller in Patients at Risk for Hepatocellular Carcinoma", Radiology, vol. 294, No. 2, Feb. 2020, 11 pages.
Kang et al., "Additional Value of Contrast-Enhanced Ultrasound (CEUS) on Arterial Phase Non-Hyperenhancement Observations (≥2 Cm) of CT/MRI for High-Risk Patients: Focusing on the CT/MRI LI-RADS Categories LR-3 and LR-4", Abdominal Radiology, vol. 45, pp. 55-63.
Kanmaniraja et al., "Liver Imaging Reporting and Data System (LI-RADS) V2018: Review of the CT/MRI Diagnostic Categories", Canadian Association of Radiologists Journal, vol. 72, No. 1, 2021, pp. 142-149.
Laroia et al., "Diagnostic Efficacy of Dynamic Liver Imaging Using Qualitative Diagnostic Algorithm Versus LI-RADS V2018 Lexicon for Atypical Versus Classical HCC Lesions: A Decade of Experience from a Tertiary Liver Institute", European Journal of Radiology Open, vol. 7, No. 100219, 2020, 18 pages.
Lee et al., "Diagnostic Performance of CT Versus MRI Liver Imaging Reporting and Data System Category 5 for Hepatocellular Carcinoma: A Systematic Review and Meta-Analysis of Comparative Studies", Liver International, vol. 40, 2020, pp. 1488-1497.
Lucatelli et al., "Intra-Procedural Dual Phase Cone Beam Computed Tomography Has a Better Diagnostic Accuracy over Pre-Procedural MRI and MDCT in Detection and Characterization of HCC in Cirrhotic Patients Undergoing TACE Procedure", European Journal of Radiology, 2019, 24 pages.
McGillen et al., "Contrast-Enhanced Ultrasonography for Screening and Diagnosis of Hepatocellular Carcinoma: A Case Series and Review of the Literature", Medicines, vol. 7, No. 51, Aug. 27, 2020, 17 pages.
Mokrane et al., "Radiomics Machine-Learning Signature for Diagnosis of Hepatocellular Carcinoma in Cirrhotic Patients with Indeterminate Liver Nodules", European Radiology, vol. 30, 2020, pp. 558-570.
Park et al., "Diagnostic Performance of LI-RADS Treatment Response Algorithm for Hepatocellular Carcinoma: Adding Ancillary Features to MRI Compared with Enhancement Patterns at CT and MRI", Radiology, vol. 296, 2020, 8 pages.
Park et al., "Abbreviated MRI with Optional Multiphasic CT as an Alternative to Full-Sequence MRI: LI-RADS Validation in a HCC-Screening Cohort", European Radiology, vol. 30, 2020, pp. 2302-2311.
Pereira et al., "Use of the LI-RADS Classification in Patients with Cirrhosis Due to Infection with Hepatitis B, C, or D, or Infected with Hepatitis B and D", Radiologia Brasileira, vol. 53, No. 1, 2020, pp. 14-20.
Pinero et al., "LI-RADS 4 or 5 Categorization May Not Be Clinically Relevant for Decision-Making Processes: A Prospective Cohort Study", Annals of Hepatology, vol. 19, 2020, 6 pages.
Puttagunta et al., "Diagnostic Accuracy of Single-Phase Computed Tomography Texture Analysis for Prediction of LI-RADS v2018 Category", Journal of Computer Assisted Tomography, vol. 44, No. 2, 2020, 6 pages.
Raatschen, H. J., "Radiological Diagnostic Workup of Liver Tumors", Internist, vol. 61, 2020, pp. 123-130.
Seo et al., "Evaluation of Treatment Response in Hepatocellular Carcinoma in the Explanted Liver with Liver Imaging Reporting and Data System Version 2017", European Radiology, vol. 30, No. 1, Jan. 2020, 22 pages.
Shropshire et al., "LI-RADS Ancillary Feature Prediction of Longitudinal Category Changes in LR-3 Observations: An Exploratory Study", Abdominal Radiology, vol. 45, 2020, pp. 3092-3102.
Tan et al., "Analysis of Comparative Performance of CEUS and CECT/MR LI-RADS Classification: Can CEUS Dichotomize LI-RADS Indeterminate Lesions on CT or MRI?", Clinical Imaging, vol. 62, Jun. 2020, pp. 63-68.
Wang et al., "Comparison of Contrast-Enhanced Ultrasound versus Contrast-Enhanced Magnetic Resonance Imaging for the Diagnosis of Focal Liver Lesions Using the Liver Imaging Reporting and Data System", Ultrasound in Medicine and Biology, vol. 46, No. 5, May 2020, pp. 1216-1223.
Woisetschläger et al., "Iterative Reconstruction Algorithm Improves the Image Quality without Affecting Quantitative Measurements of Computed Tomography Perfusion in the Upper Abdomen", European Journal of Radiology Open, vol. 7, No. 100243, 2020, 9 pages.
Zhang et al. "Performance of LI-RADS Version 2018 CT Treatment Response Algorithm in Tumor Response Evaluation and Survival Prediction of Patients with Single Hepatocellular Carcinoma After Radiofrequency Ablation", Annals of Translational Medicine, vol. 8, No. 6, 2020, 10 pages.
Kielar et al., "LI-RADS Version 2018: What is New and What Does this Mean to My Radiology Reports?", Abdominal Radiology, vol. 44, Aug. 11, 2018, pp. 41-42.
Sirlin, Claude B., "The LI-RADS Adventure-a Personal Statement", Abdominal Radiology, vol. 43, No. 1, Jan. 2018, pp. 1-2.
Piscaglia et al., "American College of Radiology Contrast Enhanced Ultrasound Liver Imaging Reporting and Data System(CEUS LI-RADS) for the Diagnosis of Hepatocellular Carcinoma: A Pictorial Essay", Ultraschall Med., vol. 38, No. 3, Jun. 2017, pp. 320-324.
International Search Report and Written Opinion received for PCT Application Serial No. PCT/US2022/022540 dated Jul. 25, 2022, 9 pages.
Shapira et al., "Liver Lesion Localisation and Classification with Convolutional Neural Networks: A Comparison Between Conventional and Spectral Computed Tomography", Biomedical Physics & Engineering Express, vol. 6, No. 015038, Jan. 31, 2020, 11 pages.
International Preliminary Report on Patentability received for PCT Application Serial No. PCT/US2022/022540 dated Oct. 12, 2023, 8 pages.
Purysko et al., "LI-RADS: A Case-based Review of the New Categorization of Liver Findings in Patients with End-Stage Liver Disease", Radio Graphics, vol. 32, 2012, 20 pages.
Jha et al., "LI-RADS Categorization of Benign and Likely Benign Findings in Patients at Risk of Hepatocellular Carcinoma: A Pictorial Atlas", American Journal of Roentgenology, vol. 203, Jul. 2014, 22 pages.
Santillan et al., "Understanding LI-RADS a Primer for Practical Use", Magnetic Resonance Imaging Clinics of North America, vol. 22, 2014, pp. 337-352.
Shah et al., "Radiological Features of Hepatocellular Carcinoma", Journal of Clinical and Experimental Hepatology, vol. 4, No. S3, Aug. 2014, 4 pages.
Anis et al., "Imaging of Hepatocellular Carcinoma: New Approaches to Diagnosis", Clinical Liver Disease, vol. 19, 2015, pp. 325-340.
Bashir et al., "Concordance of Hypervascular Liver Nodule Characterization Between the Organ Procurement and Transplant Network and Liver Imaging Reporting and Data System Classifications", Journal of Magnetic Resonance Imaging, vol. 42, No. 2, Aug. 2015, pp. 305-314.
Mitchell et al., "LI-RADS (Liver Imaging Reporting and Data System): Summary, Discussion, and Consensus of the LI-RADS Management Working Group and Future Directions", Hepatology, vol. 61, No. 3, Mar. 2015, pp. 1056-1065.
Tang et al., "Update on the Liver Imaging Reporting and Data System: What the Pathologist Needs to Know", Advances In Anatomic Pathology, vol. 22, 2015, pp. 314-322.
An et al., "Liver Imaging Reporting and Data System (LI-RADS Version 2014: Understanding and Application of the Diagnostic Algorithm", Clinical and Molecular Hepatology, vol. 22, 2016, pp. 296-307.
Chen et al., "Added Value of a Gadoxetic Acid-enhanced Hepatocyte-phase Image to the LI-RADS System for Diagnosing Hepatocellular Carcinoma", Magnetic Resonance in Medical Sciences, vol. 15, No. 1, 2016, pp. 49-59.
Potretzke et al., "Imaging Features of Biphenotypic Primary Liver Carcinoma (Hepatocholangiocarcinoma) and the Potential to Mimic Hepatocellular Carcinoma: LI-RADS Analysis of CT and MRI Features in 61 Cases", American Journal of Roentgenology, vol. 207, Jul. 2016, pp. 25-31.

(56) References Cited

OTHER PUBLICATIONS

Schellhaas et al., "LI-RADS-CEUS-Proposal for a Contrast-Enhanced Ultrasound Algorithm for the Diagnosis of Hepatocellular Carcinoma in High-Risk Populations", Ultraschall in der Medizin, 2016.
Shah et al., "Cirrhotic Liver: What's that Nodule? The LI-RADS Approach", Journal of Magnetic Resonance Imaging, vol. 43, No. 2, Feb. 2015, pp. 281-294.
Tanabe et al., "Imaging Outcomes of Liver Imaging Reporting and Data System Version 2014 Category 2, 3, and 4 Observations Detected at CT and MR Imaging", Radiology, vol. 281, No. 1, Oct. 1, 2016, 12 pages.
Zhang et al., "Classifying Ct/MR Findings in Patients with Suspicion of Hepatocellular Carcinoma: Comparison of Liver Imaging Reporting and Data System and Criteria-free Likert Scale Reporting Models", Journal of Magnetic Resonance Imaging, vol. 43, Feb. 2016, pp. 373-383.
Bae et al., "Diagnostic Accuracy of Gadoxetic Acid-enhanced MR for Small Hypervascular Hepatocellular Carcinoma and the Concordance Rate of Liver Imaging Reporting and Data System (LI-RADS)", PLoS One, 2017; 12: e0178495.
Cassinottoa et al., "Diagnosis of Hepatocellular Carcinoma: An Update on International Guidelines", Diagnostic and Interventional Imaging, vol. 98, 2017, pp. 379-391.
Chernyak et al., "Effect of Threshold Growth as a Major Feature on LI-RADS Categorization", Abdominal Radiology, 2017.
Elsayes et al., "2017 Version of LI-RADS for CT and MR Imaging: An Update1", Radio Graphics, vol. 37, No. 7, 25 pages.
Flusberg et al., "Impact of a Structured Report Template on the Quality of CT and MRI Reports for Hepatocellular Carcinoma Diagnosis", Journal of the American College of Radiology, vol. 14, 2017, 1206-1211.
Stein et al., "Implementing a Structured Reporting Initiative Using a Collaborative Multistep Approach", Current Problems in Diagnostic Radiology, vol. 46, 2017, pp. 279-299.
Goshima et al., "Gadoxetic Acid-enhanced High Temporal-resolution Hepatic Arterial-phase Imaging with View-sharing Technique: Impact on the LI-RADS Category", European Journal of Radiology, vol. 94, 2017, pp. 167-173.
Granata et al., "Major and Ancillary Magnetic Resonance Features of LI-RADS to Assess HCC: An Overview and Update", Infectious Agents and Cancer, vol. 13, No. 23, 2017, 12 pages.
Hope et al., "Change in Liver Imaging Reporting and Data System Characterization of Focal Liver Lesions Using Gadoxetate Disodium Magnetic Resonance Imaging Compared With Contrast-Enhanced Computed Tomography", Journal of Computer Assisted Tomography, vol. 41, No. 03, Nov. 1, 2017, 13 pages.
Kim et al., "Contrast-enhanced Ultrasound (Ceus) Liver Imaging Reporting And Data System (LI-RADS 2017—A Review Of Important Differences Compared To The CT/MRI System", Clinical and Molecular Hepatology, vol. 23, 2017, pp. 280-289.
Nowicki et al., "Diagnostic Imaging of Hepatocellular Carcinoma—A Pictorial Essay", Current Medical Imaging Reviews, vol. 13, No. 2, 2017, pp. 140-153.
Schellhaas et al., "Diagnostic Accuracy of Contrast-enhanced Ultrasound for the Differential Diagnosis of Hepatocellular Carcinoma: ESCULAP Versus CEUS-LI-RADS", European Journal of Gastroenterology & Hepatology, vol. 29, 2017, pp. 1036-1044.
Sofue et al., "Liver Imaging Reporting and Data System Category 4 Observations In Mri: Risk Factors Predicting Upgrade to Category 5", Journal of Magnetic Resonance Imaging, vol. 46, No. 3, 2017, pp. 783-792.
Xiong et al., "Radiologically Undetected Hepatocellular Carcinoma in Patients Undergoing Liver Transplantation: An Immunohistochemical Correlation With LI-RADS Score", The American Journal of Surgical Pathology, vol. 41, 2017, pp. 1466-1472.
Basha et al., "Does A Combined CT and MRI Protocol Enhance the Diagnostic Efficacy of LI-RADS in the Categorization of Hepatic Observations? A Prospective Comparative Study", European Society of Radiology, Jan. 24, 2018, 13 pages.
Cerny et al., "LI-RADS Version 2018 Ancillary Features at MRI", Radiographics, vol. 38, 2018, pp. 1973-2001.
Chernyak et al., "Liver Imaging Reporting and Data System (LI-RADS) Version 2018: Imaging of Hepatocellular Carcinoma in At-Risk Patients", Radiology, vol. 289, No. 3, Dec. 2018, 15 pages.
Chernyak et al., "LI-RADS(®) Algorithm: CT and MRI", Abdominal Radiology, vol. 43, 2018, pp. 111-126.
Cerny et al., "LI-RADS(®) Ancillary Fatures on CT and MRI", Abdominal Radiology, vol. 43, 2018, pp. 82-100.
Dietrich et al., "Contrast-enhanced Ultrasound: Liver Imaging Reporting and Data System (CEUS LI-RADS)", Z Gastroenterol, vol. 56, 2018, pp. 499-506.
Elsayes et al., "White Paper of the Society of Abdominal Radiology Hepatocellular Carcinoma Diagnosis Disease-focused Panel on LI-RADS v2018 for CT and MRI", Abdominal Radiology, 2018, 39 pages.
Fowler et al., "LI-RADS M (LR-M): Definite or Probable Malignancy, Not Specific for Hepatocellular Carcinoma", Abdominal Radiology, vol. 43, 2018 , pp. 149-157.
Fowler et al., "Interreader Reliability of LI-RADS Version 2014 Algorithm and Imaging Features for Diagnosis of Hepatocellular Carcinoma: A Large International Multireader Study", Radiology, vol. 286, No. 1, Jan. 2018, 14 pages.
Furlan et al., "A Radiogenomic Analysis of Hepatocellular Carcinoma: Association Between Fractional Allelic Imbalance Rate Index and the Liver Imaging Reporting And Data System (LI-RADS) Categories and Features", The British Journal of Radiology, vol. 91, No. 20170962, 2018, 6 pages.
Gupta et al., "Role of Imaging in Surveillance and Diagnosis of Hepatocellular Carcinoma", Gastroenterology Clinics of North America, vol. 47, 2018, pp. 585-602.
Kambadakone et al., "LI-RADS Technical Requirements for CT MRI, and Contrast-enhanced Ultrasound", Abdominal Radiology, vol. 43, Jan. 2018, pp. 56-74.
Kambadakone et al., "Correction to: LI-RADS Technical Requirements for CT, MRI, and Contrast-enhanced Ultrasound", Abdominal Radiology, vol. 43, Nov. 2, 2017, 240.
Kielar et al., "Locoregional Therapies for Hepatocellular Carcinoma and the New LI-RADS Treatment Response Algorithm", Abdominal Radiology, vol. 43, No. 1, Jan. 2018, 28 pages.
Kielar et al., "LI-RADS 2017: An Update", Magnetic Resonance Imaging, vol. 47, No. 6, Jun. 2018, pp. 1459-1474.
Liu et al., "Accuracy of the Diagnostic Evaluation of Hepatocellular Carcinoma with LI-RADS", Acta Radiologica, vol. 59, 2018, pp. 140-146.
Masch et al., "Radiologist Quality Assurance by Nonradiologists at Tumor Board", Journal of the American College of Radiology, vol. 15, 2018, pp. 1259-1265.
Mitchell et al., "Management Implications and Outcomes of LI-RADS-2, -3, -4, and -M Category Observations", Abdominal Radiology, vol. 43, 2018, pp. 143-148.
Narsinh et al., "Hepatocarcinogenesis and LI-RADS", Abdominal Radiology, vol. 43, 2018, pp. 158-168.
Patella et al., "CT-MRI LI-RADS v2017: A Comprehensive Guide for Beginners", Journal of Clinical and Translational Hepatology, vol. 6, 2018, pp. 222-236.
Ronot et al., "Comparison of the Accuracy of Aasld and LI-RADS Criteria for the Non-invasive Diagnosis of HCC Smaller Than 3☐Cm", Journal of Hepatology, vol. 68, 2018, pp. 715-723.
Rosiak et al., "Comparison of LI-RADS v.2017 and ESGAR Guidelines Imaging Criteria in HCC Diagnosis Using MRI with Hepatobiliary Contrast Agents", BioMed Research International, vol. 2018, No. 7465126, Jul. 15, 2018, 7 pages.
Rosiak et al., "CT/MRI LI-RADS v2017—Review of the Guidelines", Polish Journal of Radiology, vol. 83, Jul. 16, 2018, e355-e365.
Sanghvi et al., "MRI for Hepatocellular Carcinoma: A Primer for Magnetic Resonance Imaging Interpretation", Abdominal Radiology, vol. 43, May 1, 2018, pp. 1143-1151.
Santillan et al., "LI-RADS Categories: Concepts, Definitions, and Criteria", Abdominal Radiology, vol. 43, 2018, pp. 101-110.

(56) References Cited

OTHER PUBLICATIONS

Santillan et al., "LI-RADS Major Features: CT, MRI with Extracellular Agents, and MRI with Hepatobiliary Agents", Abdominal Radiology, vol. 43, 2018, pp. 75-81.
Schellhaas et al., "Interobserver and Intermodality Agreement of Standardized Algorithms for Non-invasive Diagnosis of Hepatocellular Carcinoma in High-risk Patients: CEUS-LI-RADS versus MRI-LI-RADS", European Radiology, vol. 28, 2018, pp. 4254-4264.
Schima et al., "LI-RADS v2017 for Liver Nodules: How We Read and Report", Cancer Imaging, vol. 18, No. 14, 2018, 11 pages.
Siedlikowski et al., "Implementation of LI-RADS into a Radiological Practice", Abdominal Radiology, vol. 43, 2018, pp. 179-184.
Sirlin et al., "LI-RADS: A Glimpse into the Future", Abdominal Radiology, vol. 43, 2018, pp. 231-236.
Tang et al., "Evidence Supporting LI-RADS Major Features for CT- and MR Imaging-based Diagnosis of Hepatocellular Carcinoma: A Systematic Review", Radiology, vol. 286, No. 1, Jan. 2018, pp. 29-48.
Tang et al., "LI-RADS and Transplantation for Hepatocellular Carcinoma", Abdominal Radiology, vol. 43, 2018, pp. 193-202.
Terzi et al., "Contrast Ultrasound LI-RADS LR-5 Identifies Hepatocellular Carcinoma in Cirrhosis in a Multicenter Restropective Study of 1,006 Nodules", Journal of Hepatology, vol. 68, 2018, pp. 485-492.
Wilson et al., "CEUS LI-RADS: Algorithm, Implementation, and Key Differences from CT/MRI", Abdominal Radiology, Aug. 17, 2017, 16 pages.
Wong et al., "The Effects of a Transjugular Intrahepatic Portosystemic Shunt on the Diagnosis of Hepatocellular Cancer", Plos One, Dec. 28, 2018, 10 pages.
Assadi et al., "The Need for Standardization of Nuclear Cardiology Reporting and Data System (NCAD-RADS): Learning from Coronary Artery Disease (CAD), Breast Imaging (BI), Liver Imaging (LI), and Prostate Imaging (PI) RADS", Journal of Nuclear Cardiology, vol. 26, No. 2, 2019, pp. 660-665.
Basha et al., "The Utility of Diffusion-Weighted Imaging in Improving the Sensitivity of LI-RADS Classification of Small Hepatic Observations Suspected of Malignancy", Abdominal Radiology, vol. 44, 2019, pp. 1773-1784.
Cannella et al., "Common Pitfalls When Using the Liver Imaging Reporting and Data System (LI-RADS): Lessons Learned from a Multi-Year Experience", Abdominal Radiology, vol. 44, 2019, pp. 43-53.
Chernyak et al., "Liver Imaging Reporting and Data System Version 2018: Impact on Categorization and Hepatocellular Carcinoma Staging", Liver Transplantation, vol. 25, Oct. 2019, pp. 1488-1502.
Cunha et al., "LI-RADS and Transplantation: Challenges and Controversies", Abdominal Radiology, 2019, pp. 29-42.
Elsayes et al., "User and System Pitfalls in Liver Imaging with LI-RADS", Journal of Magnetic Resonance Imaging, vol. 50, 2019, pp. 1673-1686.
Elsayes et al., "LI-RADS: A Conceptual and Historical Review from Its Beginning to Its Recent Integration into AASLD Clinical Practice Guidance", Journal of Hepatocellular Carcinoma, vol. 6, 2019, pp. 49-69.
Erkan et al., "Non-Invasive Diagnostic Criteria of Hepatocellular Carcinoma: Comparison of Diagnostic Accuracy of Updated LI-RADS with Clinical Practice Guidelines of OPTN-UNOS, AASLD, NCCN, EASL-EORTC, and KLSCG-NCC", Plos One, Dec. 10, 2019, 15 pages.
Hong et al., "Longitudinal Evolution of CT and MRI LI-RADS V2014 Category 1, 2, 3, and 4 Observations", European Radiology, vol. 29, No. 9, Sep. 2019, 20 pages.
Kamath et al., "CT/MR LI-RADS 2018: Clinical Implications and Management Recommendations", Abdominal Radiology, vol. 44, 2019, pp. 1306-1322.
Kim et al., "Comparison of International Guidelines for Noninvasive Diagnosis of Hepatocellular Carcinoma: 2018 Update", Clinical and Molecular Hepatology, vol. 25, 2019, pp. 245-263.

Kim et al., "Pitfalls and Problems to Be Solved in the Diagnostic CT/MRI Liver Imaging Reporting and Data System (LI-RADS)", European Radiology, vol. 29, 2019, pp. 1124-1132.
Kim et al., "Hepatocellular Carcinoma Versus Other Hepatic Malignancy in Cirrhosis: Performance of LI-RADS Version 2018", Radiology, vol. 291, 2019, pp. 72-80.
Kokubo et al., "A Case of Primary Clear Cell Hepatocellular Carcinoma Comprised Mostly of Clear Cells", Radiology Case Reports, vol. 14, 2019, pp. 1377-1381.
Langenbach et al., "Analysis of Lipiodol Uptake in Angiography and Computed Tomography for the Diagnosis of Malignant Versus Benign Hepatocellular Nodules in Cirrhotic Liver", European Radiology, vol. 29, 2019, pp. 6539-6549.
Ludwig et al., "Hepatocellular Carcinoma (HCC)vs. Non-HCC: Accuracy and Reliability of Liver Imaging Reporting and Data System V2018", Abdominal Radiology, vol. 44, No. 6, Jun. 2019, 33 pages.
Ludwig et al., "Expanding the Liver Imaging Reporting and Data System (LI-RADS) V2018 Diagnostic Population: Performance and Reliability of LI-RADS for Distinguishing Hepatocellular Carcinoma (HCC) from Non-HCC Primary Liver Carcinoma in Patients Who Do Not Meet Strict LI-RADS High-Risk Criteria", International Hepato-Pancreato-Biliary Association Inc., vol. 21, 2019, pp. 1697-1706.
Ludwig et al., "Diagnostic Performance of Liver Imaging Reporting and Data System (LI-RADS) V2017 in Predicting Malignant Liver Lesions in Pediatric Patients: A Preliminary Study", Paediatric Radiology, vol. 49, 2019, pp. 746-758.
Millet et al., "ACR Ultrasound Liver Reporting and Data System: Multicenter Assessment of Clinical Performance at One Year", Journal of the American College of Radiology, vol. 16, 2019, pp. 1656-1662.
Renzulli et al., "LI-RADS: A Great Opportunity Not to Be Missed", European Journal of Gastroenterology & Hepatology, vol. 31, No. 3 2018, pp. 283-288.
Shin et al., "Risk Assessment of Hepatocellular Carcinoma Development for Indeterminate Hepatic Nodules in Patients with Chronic Hepatitis B", Clinical and Molecular Hepatology, vol. 25, 2019, 10 pages.
Shropshire et al., "LI-RADS Treatment Response Algorithm: Performance and Diagnostic Accuracy", Radiology, vol. 292, 2019, 9 pages.
Son et al., "Validation of US Liver Imaging Reporting and Data System Version 2017 in Patients at High Risk for Hepatocellular Carcinoma", Radiology, vol. 292, 2019, pp. 390-397.
Tang et al., "Introduction to the Liver Imaging Reporting and Data System for Hepatocellular Carcinoma", Clinical Gastroenterology and Hepatology, vol. 17, 2019, pp. 1228-1238.
Tang et al., "Predictors and Cumulative Frequency of Hepatocellular Carcinoma in High and Intermediate LI-RADS Lesions: A Cohort Study from a Canadian Academic Institution", Annals of Surgical Oncology, vol. 26, 2019, pp. 2560-2567.
Pol et al., "Accuracy of the Liver Imaging Reporting and Data System in Computed Tomography and Magnetic Resonance Image Analysis of Hepatocellular Carcinoma or Overall Malignancy-a Systematic Review", Gastroenterology, vol. 156, No. 4, Mar. 2019, pp. 976-986.
Violi et al., "Radiological Diagnosis and Characterization of HCC", Journal, 2019, pp. 71-92.
Voizard et al., "Assessment of Hepatocellular Carcinoma Treatment Response with LI-RADS: A Pictorial Review", Insights into Imaging, vol. 10, No. 121, 2019, 22 pages.
Wang et al., "Deep Learning for Liver Tumor Diagnosis Part II: Convolutional Neural Network Interpretation Using Radiologic Imaging Features", European Radiology, vol. 29, No. 7, 2019, 19 pages.
Razek et al., "Liver Imaging Reporting and Data System Version 2018: What Radiologists Need to Know", Journal of Computer Assisted Tomography, vol. 44, No. 2, 2020, pp. 168-177.
Amorim et al., "Critical Review of HCC Imaging in the Multidisciplinary Setting: Treatment Allocation and Evaluation of Response", Abdominal Radiology, vol. 45, pp. 3119-3128.

(56) References Cited

OTHER PUBLICATIONS

Bartolotta et al., "CEUS LI-RADS: A Pictorial Review", Insights into Imaging, vol. 11, No. 9, 2020, 13 pages.

Bousabarah et al., "Automated Detection and Delineation of Hepatocellular Carcinoma on Multiphasic Contrast-Enhanced MRI Using Deep Learning", Abdominal Radiology, vol. 46, No. 1, Jan. 21, 2021, 20 pages.

* cited by examiner

FIG. 2

Example Feature Detection Metrics

| | Arterial | Portal Venous | Delayed |
|---|---|---|---|
| Maximum APHE | ΔHU=(+)203, a=(-)116 | no | no |
| Washout | no | ΔHU=(-)122, a=(-)192 | ΔHU=(-)184, a=(-)192 |
| Capsule | no | ΔHU=(+)30, a=(-)192 | ΔHU=(+)40, a=(-)192 |

Table 200

ARTIFICIAL INTELLIGENCE ASSISTED DIAGNOSIS AND CLASSIFICATION OF LIVER CANCER FROM IMAGE DATA

RELATED APPLICATION

This application claims priority to U.S. Provisional Application Ser. No. 63/169,665 filed Apr. 1, 2021 and titled "ARTIFICIAL INTELLIGENCE ASSISTED DIAGNOSIS AND CLASSIFICATION OF LIVER CANCER FROM IMAGE DATA," the entirety of which application is incorporated herein by reference.

TECHNICAL FIELD

This application relates to medical image processing and more particularly to artificial intelligence (AI) aided diagnosis systems and methods for diagnosing and classifying liver cancer.

BACKGROUND

Liver cancer is the fifth most common cancer worldwide and the third most common cause of death from cancer. Hepatocellular carcinoma (HCC) is the most common primary liver cancer in adults. It is often hard to find liver cancer early because signs and symptoms often do not appear until it is in its later stages. Small liver tumors are hard to detect on a physical exam because most of the liver is covered by the right rib cage. By the time a tumor can be felt, it might already be quite large. In addition, the liver is a complex organ with two vascular supplies where disease can develop. This complexity makes it one of the few organs where accurate diagnostics can only be achieved based on image analysis. Providing tools and workflows to support clinicians in reading liver images and evaluating specific liver features is essential in achieving this goal.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later.

In one or more embodiments described herein, systems, computer-implemented methods, apparatus and/or computer program products are described that provide computer-assisted diagnostics and classification of liver cancer. Specifically, the innovation relates to assessment of liver exams and features of a liver lesion using medical image processing algorithms that leverage AI and machine learning (ML) algorithms, and their integration into a computer-aided clinical diagnosis and classification system for liver cancer.

According to an embodiment, a system is provided that comprises a memory that stores computer executable components, and a processor that executes the computer executable components stored in the memory. The computer executable components comprise a rendering component that renders medical images of a liver of a patient in a graphical user interface that facilitates evaluating liver imaging exams, and a lesion detection component that identifies an observation on the liver as depicted in one or more of the medical images. The computer executable components further comprise a feature detection component that analyzes the observation as depicted in the one or more medical images using one or more feature detection algorithms to characterize defined imaging features associated with the observation, wherein the rendering component further renders results of the feature detection component via the graphical user interface.

In some implementations, the computer executable components further comprise a scoring component that determines a hepatocellular carcinoma (HCC) classification score for the observation based on characterization of the defined imaging features, wherein the rendering component further renders the HCC classification score via the graphical user interface. The scoring component can employ one or more deep learning models to determine the HCC classification score. In various implementations, the defined imaging features can include, but are not limited to, arterial phase hyperenhancement (APHE), washout appearance, enhancing capsule appearance, size, and threshold growth. The feature detection component can determine the defined imaging features based one or more of, enhancement pattern information, morphological information and texture information associated with the observation.

In some implementations, the feature detection component determines presence or absence of at least some of the defined imaging features based on confidence scores associated with the outputs generated by the one or more feature detection algorithms. The computer executable components can further comprise a reporting component that generates a warning notification in response to an inability of the feature detection component to accurately characterize the defined imaging features based on the confidence scores being outside a defined confidence region. The rendering component can further provide the warning notification via the graphical user interface in association with visual and numerical tools assessment tools of the medical imaging application that facilitate manual assessment of the medical images.

In one or more implementations, the lesion detection component employs a lesion segmentation model to automatically identify the observation in the one or more medical images. Additionally, or alternatively, the lesion detection component identifies the lesion based on reception of user input via the graphical user interface defining a diameter of the observation as depicted in at least one medical image of the medical images.

In some implementations, the medical images comprise different series of medical images associated with different hepatic vascular phases, and the computer executable component further comprise a phase identification component that identifies the different series of the medical images as stored in one or more data storage units, wherein the rendering component renders the different series in separate windows of the graphical user interface. The computer executable components can further comprise a registration component that registers respective images included in the different series based on an extracted shape of the liver using one or more image registration algorithms.

The computer executable components can further comprise a reporting component that generates an assessment report of health of the liver based on the observation, the HCC classification score and the characterization of the defined imaging features. The computer executable components can further comprise an assessment tools component that provides one or more assessment tools via the graphical user interface that facilitate manually reviewing and receiving user input in association with generating the assessment report in accordance with a guided workflow.

In some embodiments, elements described in the disclosed systems can be embodied in different forms such as a computer-implemented method, a computer program product, or another form.

DESCRIPTION OF THE DRAWINGS

FIG. 2 provides a table defining some example feature detection metrics that can be used to detect and characterize imaging features in accordance with one or more embodiments of the disclosed subject matter.

DETAILED DESCRIPTION

Figure 1:
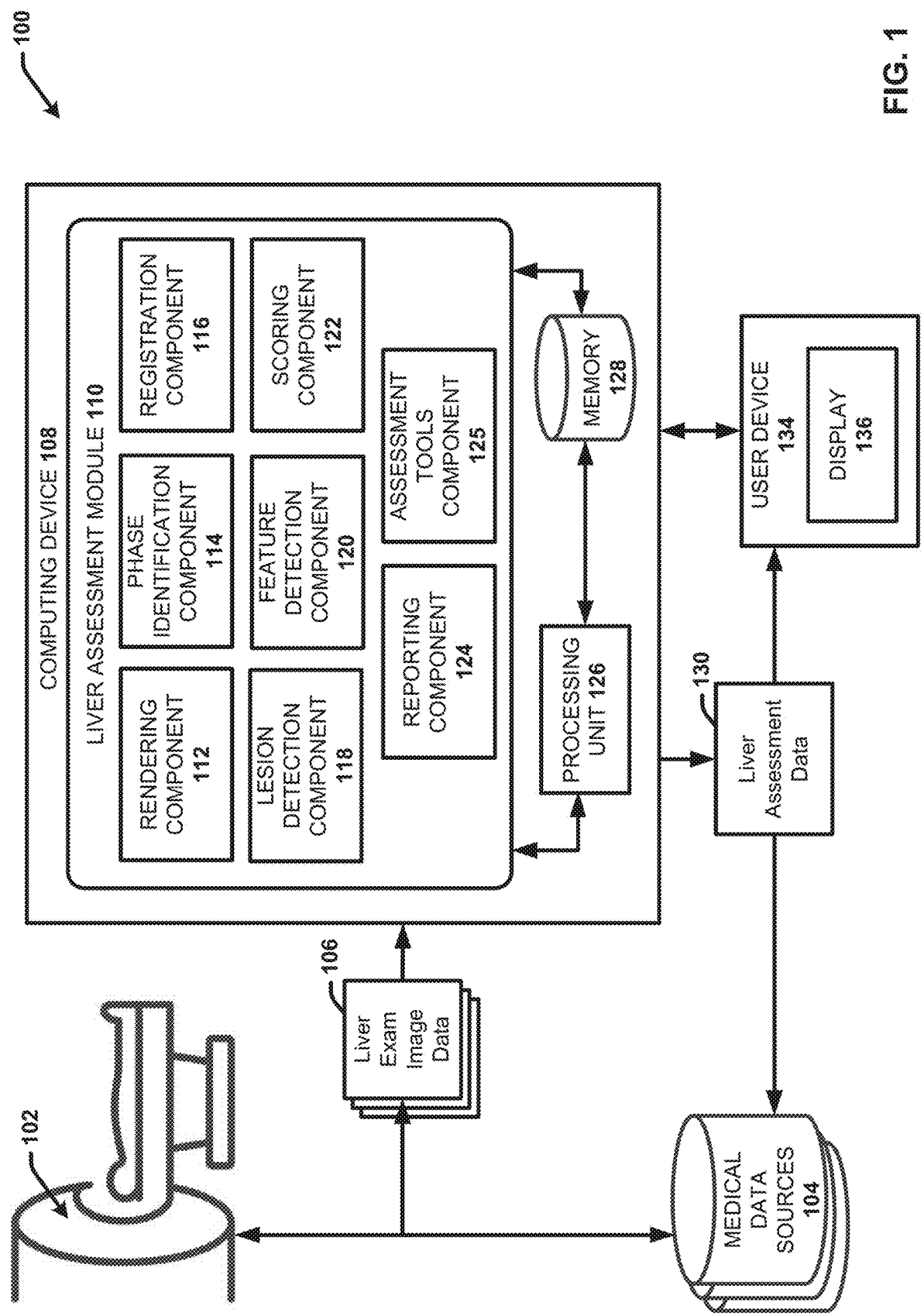
FIG. 1 illustrates a block diagram of an example, non-limiting system that facilitates evaluating liver imaging exams and diagnosing liver cancer using AI analytics in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The disclosed subject matter is directed to systems, computer-implemented methods, apparatus and/or computer program products that facilitate diagnosing and classifying liver cancer using image analysis with AI analytics. More specifically, the disclosed subject matter provides AI tools that facilitate assessment of liver exams and lesion features as depicted in medical image data. In various embodiments, these AI tools include AI/ML algorithms configured to process multiphase computed tomography (CT) images and/or multiphase magnetic resonance (MR) images captured of the liver. In this regard, multiphase images of the liver refer to images or image series captured at different hepatic phases which can vary depending on the capture modality (e.g., vary for CT and MR). However, the disclosed techniques can be extended to other imaging modalities.

In some embodiments, these AI/ML algorithms include one or more algorithms that analyze multiphase image data and automatically identify the different series associated with each of the different hepatic vascular phases captured. These AI tools can further include one or more image processing algorithms that perform automated series registration based on the shape of the liver as depicted in the respective series. These AI tools can further include one or more segmentation algorithms configured to identify and segment abnormalities (e.g., lesions and potential lesions) depicted in the image data. Additionally, or alternatively, the disclosed techniques can employ a reviewer assisted abnormality detection process that provides semi-automatic contouring of user defined liver observations.

These AI tools can further include one or more algorithms configured to detect and characterize defined imaging features associated with a liver observation included in the image data. For example, these feature detection algorithms can be configured to evaluate the portions of the image data associated with the detected/segmented observation and determine information regarding (but not limited to) APHE, enhancing capsule appearance, observation size, and threshold growth. In some embodiments, these feature detection algorithms can be configured to infer whether one or more of these features are present or absent in the observation. In other embodiments, the feature detection algorithms can be configured to infer a measurable value for one or more of features.

These AI/ML algorithms can further include one or more diagnostic algorithms configured to generate a diagnosis evaluation for a detected/segmented observation. For example, in various embodiments, the one or more diagnostic algorithms can classify or score the pathology of an observation with a value representative of whether and to what degree the observation is HCC based at least in part on the results of the one or more feature detection algorithms. In some embodiments, the one or more diagnostic algorithms can apply the Liver Imaging Reporting and Data System (LI-RADS®) ontology in association with evaluating and scoring liver observations. The LI-RADS® provides a standardized protocol for the interpretation and reporting of observations seen on studies performed in patients at risk for development of HCC. The LI-RADS protocol categorizes observations on a spectrum from definitely benign to definitely HCC.

The disclosed subject matter further provides systems and methods for integrating these AI tools into clinical workflows to support and guide clinical review of liver imaging exams and diagnosis of liver cancer. In various embodiments, these AI tools can be integrated into a medical imaging review application that provides for viewing medical images and generating diagnostic evaluations based on the medical images. For instance, the medical imaging review application can be deployed as a web-application, a native application, a hybrid application or the like. In this regard, the medical imaging review application can be designed for usage by clinicians/radiologist to facilitate their diagnostic reporting workflows with increased accuracy and efficiency. The application and/or the AI/ML algorithms can also be used by AI model developers to facilitate annotating medical images, reviewing model performance accuracy and model updating.

In some embodiments in which these AI tools are integrated into a medical imaging application to facilitate computer aided diagnostic reporting in accordance with guided liver assessment workflows. The application can include (or be coupled to) logic that provides for loading medical images included in a selected liver imaging exam (e.g., for a particular patient) and displaying them in a graphical user interface presented to the reviewer. In implementations in which the liver imaging exam includes multiphase image data captured of the liver at different hepatic vascular phases, the application can employ one or more phase identification algorithms to identify and separate the images into different series corresponding to the different hepatic vascular phases. The application can further be configured to load the different series in different windows of the graphical user interface. The application can also perform automatic series registration based on the shape of the liver in the images using one or more image registration algorithms.

In addition to presenting the different liver exam series to the reviewer, the application can further provide a variety of assessment tools that facilitate identifying and evaluating untreated observations that appear in one or more of the images. In some embodiments, the application can automatically identify and segment the untreated observations depicted in the image data using one or more segmentation models. Additionally, or alternatively, the application can employ a reviewer assisted abnormality detection process that provides semi-automatic contouring of user defined liver observations based on user mark-up of the image data as displayed via the graphical user interface.

The application can further automatically detect and characterize defined imaging features associated with an identified/extracted liver observation included in the image data using one or more feature detection algorithms. In some embodiments, the application can also mark-up the image data (e.g., with highlighting, with color, with indica point to the feature, etc.) that depicts the detected imaging feature and provide information describing the detected imaging features (e.g., calculated imaging metrics for the detected features). The application can further generate an inferred/estimated diagnostic evaluation for a detected/segmented observation using one or more diagnostic algorithms. For example, the inferred/estimated diagnosis evaluation can include an HCC classification score representative of whether and to what degree the observation is HCC. The application can further present the results of the one or more feature detection algorithms and the one or more diagnostic algorithms to the review for their review. The application can also allow the reviewer to edit and/or accept the automated liver evaluation and generate a corresponding report which can be associated with the patient's electronic medical record, exported, shared and so on.

The term "observation" as applied to liver images is defined herein as an area distinctive compared to background liver imaging. An observation may be a true lesion (if there is a corresponding pathologic abnormality) or a pseudolesion (if there is not). An observation generically applies to any apparent abnormality detected at imaging. As a generic term, it is preferred over lesion or nodule, since some observations (e.g., perfusion alterations, artifacts, etc.) may represent pseudolesion rather than true lesions or nodules. The term "lesion" is used herein to refer to an area of parenchyma that is abnormal. A lesion can include a mass or a non-mass lesion. The term "treated lesion" is user herein to refer to a lesion treated by locoregional therapy.

The term "image inferencing model" is used herein to refer to an AI/ML model configured to perform an image processing or analysis task on images. The image processing or analysis task can vary. In various embodiments, the image processing or analysis task can include, (but is not limited to): a segmentation task, an image reconstruction task, an object recognition task, a motion detection task, a video tracking task, an optical flow task, and the like. The image inferencing models described herein can include 2D image processing models as well as 3D image processing models. The image processing model can employ various types of AI/ML algorithms, including (but not limited to): deep learning models, neural network models, deep neural network models (DNNs), convolutional neural network models (CNNs), generative adversarial neural network models (GANs) and the like. The terms "image inferencing model," "image processing model," "image analysis model," and the like are used herein interchangeably unless context warrants particular distinction amongst the terms. The terms "model" and algorithm are used herein interchangeably unless context warrants particular distinction amongst the terms.

The term "image-based inference output" is used herein to refer to the determination or prediction that an image processing model is configured to generate. For example, the image-based inference output can include a segmentation mask, a reconstructed image, an adapted image, an annotated image, a classification, a value, or the like. The image-based inference output will vary based on the type of the model and the particular task that the model is configured to perform. The image-based inference output can include a data object that can be rendered (e.g., a visual data object), stored, used as input for another processing task, or the like. The terms "image-based inference output", "inference output" "inference result" "inference", "output", "predication", and the like, are used herein interchangeably unless context warrants particular distinction amongst the terms.

As used herein, a "medical imaging inferencing model" refers to an image inferencing model that is tailored to perform an image processing/analysis task on one or more medical images. For example, the medical imaging processing/analysis task can include (but is not limited to): disease/condition classification, disease region segmentation, organ segmentation, disease quantification, disease feature characterization, disease/condition staging, risk prediction, temporal analysis, anomaly detection, anatomical feature characterization, medical image reconstruction, and the like. The terms "medical image inferencing model," "medical image processing model," "medical image analysis model," and the like are used herein interchangeably unless context warrants particular distinction amongst the terms.

The types of medical images processed/analyzed by the medical image inferencing models described herein can include images captured using various types of image capture modalities. For example, the medical images can include (but are not limited to): radiation therapy (RT) images, X-ray (XR) images, digital radiography (DX) X-ray images, X-ray angiography (XA) images, panoramic X-ray (PX) images, computerized tomography (CT) images, mammography (MG) images (including a tomosynthesis device), a magnetic resonance imaging (MR) images, ultrasound (US) images, color flow doppler (CD) images, position emission tomography (PET) images, single-photon emissions computed tomography (SPECT) images, nuclear medicine (NM) images, and the like. The medical images can also include synthetic versions of native medical images such as synthetic X-ray (SXR) images, modified or enhanced versions of native medical images, augmented versions of native medical images, and the like generated using one or more image processing techniques. The medical imaging processing models disclosed herein can also be configured to process 3D images.

A "capture modality" as used herein refers to the specific technical mode in which an image or image data is captured using one or more machines or devices. In this regard, as applied to medical imaging, different capture modalities can include but are not limited to: a 2D capture modality, a 3D capture modality, an RT capture modality, a XR capture modality, a DX capture modality, a XA capture modality, a PX capture modality a CT, a MG capture modality, a MR capture modality, a US capture modality, a CD capture modality, a PET capture modality, a SPECT capture modality, a NM capture modality, and the like.

The term "multiphase" as used herein with respect to medical imaging refers to capture of image data of the same patient/anatomy using a same capture modality yet under different conditions. In various embodiments, the different conditions can include different acquisition protocols, different acquisition prescription planes (e.g., capture orientation), and/or different physiological phases. The resulting image data can include different sets or series of medical images captured in association with each of the different phases.

In various embodiments, the different physiological phases can be based on contrast injection. For example, the dual vascular supply of liver (75% portal venous and 25% hepatic arterial) results in sequential opacification of hepatic arteries, portal veins, and hepatic veins after injection of intravenous contrast. Different tissues and structures reach peak enhancement at different times. This allows the acquisition of images during different time ranges or "dynamic phases" to highlight these differences. In this regard, multiphase MR and/or multiphase CT can refer to image acquisition at sequential time ranges before and after contrast administration. While these phases are a continuum, they are described as distinct time ranges for simplicity and clinical utility. As applied to liver imaging in MR and CT for cancer detection/evaluation, the phases are selected to achieve adequate lesion to background contrast and facilitate characterization of imaging features.

In some embodiments, multiphase MR and/or multiphase CT can include image data captured over two or more of the following phases: pre-contrast phase (or unenhanced phase), intravenous (IV) phase (IVP), arterial phase (AP), early AP, late AP, extracellular phase (ECP), portal venous phase (PVP), delayed phase (DP), transitional phase (TP), hepatobiliary phase (HBP), and variants thereof.

As used herein, a "3D image" refers to digital image data representing an object, space, scene, and the like in three dimensions, which may or may not be displayed on an interface. 3D images described herein can include data representing positions, geometric shapes, curved surfaces, and the like. In an aspect, a computing device, such as a graphic processing unit (GPU) can generate a 3D image based on the data, performable/viewable content in three dimensions. For example, a 3D image can include a collection of points represented by 3D coordinates, such as points in a 3D Euclidean space (e.g., a point cloud). The collection of points can be associated with each other (e.g. connected) by geometric entities. For example, a mesh comprising a series of triangles, lines, curved surfaces (e.g. non-uniform rational basis splines ("NURBS")), quads, n-grams, or other geometric shapes can connect the collection of points. In an aspect, portions of the mesh can include image data describing texture, color, intensity, and the like.

In various embodiments, captured 2D images (or portions thereof) can be associated with portions of the mesh. A 3D image can thus be generated based on 2D image data, 2D sensory data, sensory data in combination with raw 2D data, 3D spatial data (e.g. spatial depth and distance information), computer generated positional data, and the like. In an aspect, data used to generate 3D images can be collected from scans (e.g. utilizing sensors) of real-world scenes, spaces (e.g. houses, office spaces, outdoor spaces, etc.), objects (e.g. furniture, decorations, goods, etc.), anatomical regions of the body, and the like. Data can also be generated based on computer implemented 3D modeling systems. In some embodiments, a 3D image can be or include a 3D volume image that provides a 3D representation or model of an object or environment generated from a plurality of 2D images captured along different planes. For example, a CT volume image can be or correspond to a 3D representation of an anatomical region of a patient generated/computed from a series of CT scan slices captured along different planes. In this regard, as applied to medical imaging, a 3D image can be or include a 3D volume image of anatomical region of a patient.

In this regard, a 3D medical image refers to a 3D representation of an anatomical region of a patient. In some implementations, a 3D medical image can be captured in 3D directly by the acquisition device and protocol. In other implementations, a 3D medical image can comprise a generated image that was generated from 2D and/or 3D image data captured of the anatomical region of the patient. Some example 3D medical images include 3D volume images generated from CT image data, MRI image data, and US image data.

It is noted that the terms "3D image," "3D volume image," "volume image," "3D model," "3D object,", "3D reconstruction," "3D representation," "3D rendering," and the like are employed interchangeably throughout, unless context warrants particular distinctions among the terms. It should be appreciated that such terms can refer to data representing an object, an anatomical region of the body, a space, a scene, and the like in three dimensions, which may or may not be displayed on an interface. The terms "3D data," can refer to data utilized to generate a 3D image, data describing a 3D image, data describing perspectives or points of view of a 3D image, capture data (e.g. sensory data, images, etc.), meta-data associated with a 3D image, and the like. It is noted that the term a "2D image" as used herein can refer to data representing an object, an anatomical region of the body, a space, a scene, and the like in two dimensions, which may or may not be displayed on an interface.

The term "native" image is used herein to refer to an image in its original capture form and/or its received form prior to processing by the disclosed systems. In this regard, a native 3D image refers to a 3D image in its received state prior to pre-projection processing, transformation processing, projection processing, and post-projection/transformation processing. For example, a native 3D image can include a received 3D volume image, such a s CT volume image. The term "synthetic" image is used herein to distinguish from native images and refers to an image generated or derived from a native image using one or more transformation processing techniques disclosed herein. In various embodiments, a synthetic image refers to a second modality image generated and/or derived from a first modality image. For example, in some embodiments, the second modality image comprises a 2D modality image (e.g., an XR modality) and the first modality image comprises a 3D modality image (e.g., a CT modality).

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a block diagram of an example, non-limiting system 100 that facilitates evaluating liver imaging exams and diagnosing liver cancer using AI analytics in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

For example, system 100 includes a computing device 108 that comprises a liver assessment module 110 that can be and/or include various computer executable components. In the embodiment shown, these computer executable components include a rendering component 112, a phase identification component 114, a registration component 116, a lesion detection component 118, a feature detection component 120, a scoring component 122, a reporting component 124 and an assessment tools component 125. These computer/machine executable components (and other described herein) can be stored in memory associated with the one or more machines. The memory can further be operatively coupled to at least one processor, such that the components can be executed by the at least one processor to perform the operations described. For example, in some embodiments, these computer/machine executable components can be stored in memory 128 of the computing device 108 which can be coupled to processing unit 126 for execution thereof. Examples of said and memory and processor as well as other suitable computer or computing-based elements, can be found with reference to FIG. 14, and can be used in connection with implementing one or more of the systems or components shown and described in connection with FIG. 1 or other figures disclosed herein.

System 100 further depicts a medical imaging device 102, one or more medical data sources 104 and a user device 134. The type of the medical imaging device 102 can vary. In some embodiments, the medical imaging device 102 can include an MRI machine. In other embodiments, the medical imaging device 102 can include a CT machine. Other medical imaging devices are envisioned. In either of these embodiments, the medical imaging device 102 can capture/generate liver exam image data 106 that provides medical images of a patient's liver. In some embodiments, the liver exam image data 106 can include multiphase MR data captured of the patient's liver at two or more hepatic vascular phases. In other embodiments, the liver exam image data 106 can include multiphase CT data captured of the patient's liver at two or more hepatic vascular phases. In either of these embodiments, the liver exam data 106 can include two or more different series of images captured of the patient's liver under different conditions. Additionally, or alternatively, the liver exam image data 106 can include medical images captured of the patient's liver using a variety of other (other than MR and CT) capture modalities under a variety of different conditions.

In some embodiments, the computing device 108 can receive and process (e.g., by the liver assessment module 110) liver exam image data 106 provided directly from the medical imaging device 102. In other embodiments, the computing device 108 can receive and process (e.g., by the liver assessment module 110) liver exam image data 106 provided by one or more medical data sources 104. For example, the one or more medical data sources 104 can include a medical image storage system that stores medical images (e.g., captured by the medical imaging device 102 and/or other acquisition devices), such as a Picture Archiving and Communication System (PACS) and/or a Vendor Neutral Archive (VNA). In either of these embodiments, the computing device 108, the medical imaging device 102 and the one or more medical data sources 104 can be communicatively coupled via one or more wired or wireless communication networks (e.g., a wide area network (WAN), a local area network (LAN), or the like).

In the embodiment shown, the user device 134 can correspond to a computing device employed by a user (e.g., a clinician, a radiologist, a technician, or the like) to view the liver exam image data 106 and/or employ one or more features and functionalities provided by the liver assessment module 110. For example, in some embodiments, the computing device 108 can correspond to an application server that provides at least some features and functionalities of the liver assessment module 110 to the user device 134 via a network accessible platform, such as a web-application or the like. With these embodiments, the user device 134 can access the features and functionalities of the liver assessment module 110 as a web-application using a suitable browser network. The client device 134 can include a display 136 for rendering the liver exam image data 106 in a graphical user interface provide by the web-application. Additionally, or alternatively, system 100 can employ a local deployment architecture wherein the liver assessment module 110 is deployed at the user device 134 as a local/native imaging application. Still in other embodiments, one or more components of the liver assessment module 110 can be deployed at different computing devices/machines in a distributed computing environment and communicatively coupled via one or more networks. Various alternative deployment architecture variations can also be used.

Regardless of the deployment architecture used, the liver assessment module 110 can include rendering component 112 to provide for rendering the liver exam image data 106 in a graphical user interface displayed via a device display (e.g., display 136). For example, in some embodiments, the rendering component 112 can render the liver exam image data 106 in association with utilization of medical imaging application provided by the liver assessment module 110 and the computing device 108 and/or provided by another system. With these embodiments, one or more features and functionalities of the liver assessment module 110 can be integrated with the medical imaging application. The medical imaging application can provide a variety of computer-aided diagnostic tools that facilitate reviewing and evaluating liver exams in accordance with one or more guided workflows. For instance, the medical imaging application can provide for selecting a particular liver exam study for viewing/evaluating. Based on selection of the imaging study, the rendering component 112 can access and load the corresponding images for displaying in application graphical user interface. As described in greater detail below, the rendering component 112 can provide a 'smart' visualization functionality that automatically configures the layout of the medical images in the graphical user interface and the tools for assessing the medical images based on automatically identified hepatic phases in the series and other features extracted from the medical images. The tools for assessing the medical images (e.g., provided/defined by the assessment tools component 125) can also include automatic and semi-automatic assessment tools (e.g., automatic and/or semi-automatic lesion detection and classification, automatic and/or semi-automatic lesion feature characterization, automatic and/or semi-automatic lesion feature annotation, other tools described infra) that guide the manual review and assessment process in accordance with defined workflow steps. In this regard, the tools assessment component 125 can define the logic/functions of the one or more of the automated and/or interactive application functions/tools of the medical imaging application described herein with reference to FIGS. 3-9.

Figure 3:
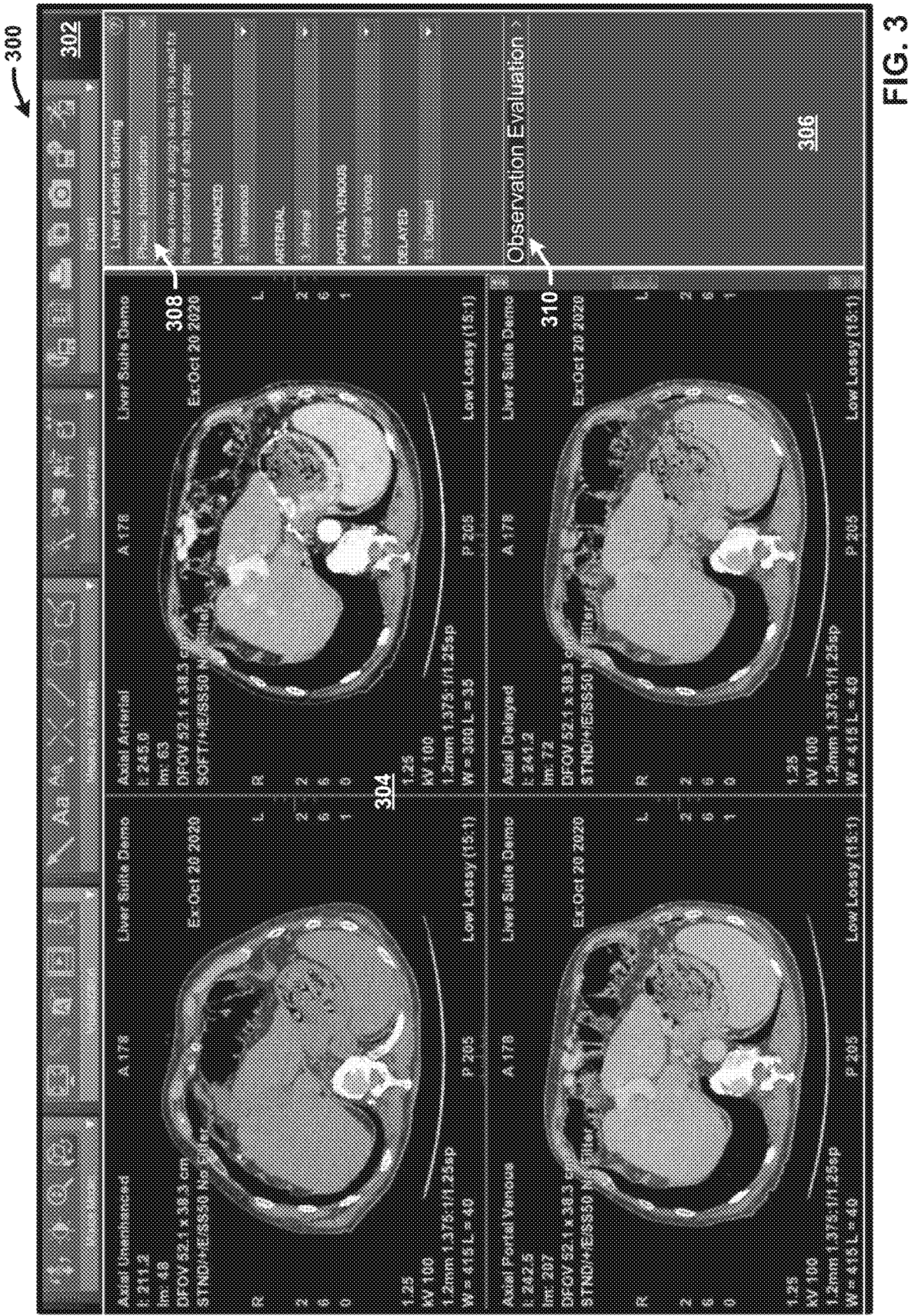
FIGS. 3-9 presents example graphical user interfaces of an example medical imaging application that facilitates evaluating liver imaging exams and diagnosing liver cancer using AI analytics in accordance with one or more embodiments of the disclosed subject matter.

FIG. 3 presents an example graphical user interface 300 that can be generated/rendered by the rendering component 112 in response to initial selection of a multiphase liver imaging study for a patient in association with usage of such a medical imaging application. The graphical user interface 300 includes an upper toolbar 302 with different tabs corresponding to different application tools/functions and a visualization area 304 that includes the rendered liver exam image data. The graphical user interface 300 further includes a right-side panel 306 that provides various controls and tools for evaluating observations depicted in the liver images. In the embodiment shown, these tools include a phase identification tool 308 and an observation evaluation tool 310. The features and functionalities of the phase identification tool 308 and the observation evaluation tool 310 are described in greater detail below. In some embodiments, the assessment tools component 125 can define the computer executable instructions/operations of the phase identification tool and the observation evaluation tool 310.

In the embodiment shown in FIG. 3, the visualization display area 304 includes four different windows that provide different images of the liver. In this example, the different windows present different series of a multiphase CT liver exam from the axial perspective. In particular, the upper left window presents the unenhanced phase series, the upper right window presents the arterial phase series, the lower left window presents the portal venous series, and the lower right window presents the delayed series. In various embodiments, the entirety of the images included in each series can be independently viewed and scrolled in each of the four windows. For example, the initial image shown for each series can include a default selected image, such as the first image in each series, the middle image in each series, or the like.

With reference to FIGS. 1 and 3, the phase identification component 114 can provide for automatically identifying and classifying different image series included in the liver exam image data 106 corresponding to different phases, such as the different series corresponding to the different phases shown in the four different windows of the graphical user interface 300 shown in FIG. 3. In some implementations, the phase identification component 114 can automatically separate the different image series from one another to enable rendering of the different series in different windows as shown in FIG. 3. The rendering component 112 can thus tailor the number and arrangement of the windows and the images displayed therein based on the different phases identified by the phase identification component 114. In some embodiments, the phase identification component 114 can separate a multiphase imaging study into different series corresponding to different phases as a pre-processing step prior to launching and loading of the imaging study. With these embodiments, the different series can be separated and stored (e.g., at the one or more medical data sources) as separate files prior to loading and rendering by the rendering component 112. In other embodiments, the phase identification component 114 can process the liver exam image data 106 to automatically identify, classify and separate the images into different series corresponding to different phases at the time of rendering.

To facilitate this end, the phase identification component 114 can employ one or more phase identification algorithms configured to evaluate the liver exam image data 106 and/or metadata associated therewith (e.g., regarding timing of capture, timing of contrast injection, capture protocols implemented, etc.) and distinguish between images corresponding to different pre-defined hepatic vascular phases. For example, the phase identification component 114 can evaluate a set of images for a single multiphase CT and/or MR image exam/study of the liver to identify different subsets of the images (i.e., image series) corresponding to a pre-contrast phase (or unenhanced phase), an IVP, an AP, an early AP, a late AP, an ECP, a PVP, a DP, a TP, a HBP, and variants thereof. In some embodiments, the one or more phase identification algorithms can be or include one or more image inferencing models trained on hundreds or thousands (or more) of multiphase CT and/or MR liver images using supervised or semi-supervised machine learning to identify liver image corresponding to the distinct phases based on distinguishing image features associated with each phase. The one or more phase identification algorithms can be stored in memory 128 and/or another accessible data storage device.

In one or more embodiments, the phase identification tool 308 can provide for manually reviewing and adjusting the results of the phase identification component 114. For example, in the embodiment shown, the phase identification tool 308 includes at least one drop-down selection menu can be used to review the images in automatically identified/separated phase, re-assign individual images to different phases, and/or remove images included in a particular phase. For example, the phase identification tool 308 provides separate drop-down menus for each identified phase (e.g., unenhanced, arterial, portal venous and delayed) which indicate the number of images included in each separated phase series (e.g., 2, 3, 4 and 13, respectively). Selection of the drop-down menu for a particular phase can result in rendering of an interactive list view of the images (e.g., with a text string image name/identifier) included in the phase which can be directly edited via the phase identification tool 308 (e.g., to add/remove images, re-assign individual images to a different phase, and so on).

With reference again to FIG. 1, the registration component 116 can perform series registration in association with rendering of the images and/or prior to further processing of the images by the lesion detection component 118 and the feature detection component 120. In some embodiments, the image registration process can involve shifting or morphing the geometry (e.g., shape, size, orientation, field of view, zoom level, etc.) of the images within a same series (separated by phase distinctions) to be consistent or in alignment with one another based on the shape of the liver. Additionally, or alternatively, the image registration process can involve shifting or morphing the geometry of the images of the different series to be consistent or in alignment with one another based on the shape of the liver. In this regard, the result of the registration process is a transformation of all the images included in the exam, and/or all the images included in a same series to be geometrically consistent relative to the size, shape and orientation of the liver.

To facilitate this end, the registration component 116 can employ one or more preconfigured image registration algorithms configured to automatically detect the shape, size and position of the liver as depicted in all images that are registered (e.g., all images in the exam, and/or all images within a same series). In some embodiments, the one or more image registration algorithms can include or employ one or more image inferencing models trained on hundreds or thousands (or more) of multiphase CT and/or MR liver images using supervised or semi-supervised machine learning to perform liver segmentation to accurately detect the shape, size and position of the liver as depicted in the different images. The one or more image registration algorithms can also be stored in memory 128 and/or another accessible data storage device.

The lesion detection component 118 can automatically (without manual involvement) and/or semi-automatically (with some manual involvement) identify and segment observations (e.g., lesions and potential lesions) included in the liver exam image data 106. In this regard, in some embodiments, the lesion detection component 118 can perform automatic observation identification and segmentation using one or more observation segmentation algorithms. The one or more observation segmentation algorithms can include or employ one or more image inferencing models trained on hundreds or thousands (or more) of multiphase CT and/or MR liver images using supervised or semi-supervised machine learning to perform observation segmentation to accurately detect the shape, size and position of lesions and potential lesions as depicted one or more of the images included in the liver exam image data 106. These observation segmentation algorithms can learn and exploit correlations of observation features detected in similar images from different liver exams (e.g., for different patients) as well as correlations between observation features included in different phase series of the same study/exam. The one or more observation segmentation algorithms can also be stored in memory 128 and/or another accessible data storage device.

In some implementations of these embodiments, the lesion detection component 118 can further automatically generate and apply (e.g., without manual involvement) graphical mark-ups on the corresponding images in which lesions and potential lesions were automatically detected and segmented. For example, the graphical mark-ups can include observation masks and/or a shape outline around the perimeter of the observation as displayed in the graphical user interface. The lesion detection component 118 can also determine geometrical parameters of detected lesions and potential lesions. For example, the lesion detection component 118 can determine the size, shape, diameter, relative position (e.g., relative to one or more anatomical features of reference), etc. of detected lesions and potential lesions. This automatically generated lesion segmentation/geometry information can also be presented to the reviewer via the medical imaging application. The medical imaging application can also provide tools for manually editing the segmentation and/or geometry information determined by the lesion detection component 118.

In accordance with the semi-automated lesion detection protocol, the medical imaging application can provide an auto-contouring tool that allows a reviewer to manually identify, mark and define observations detected in the rendered images via the graphical user interface. In some implementations, the auto-contouring tool can require minimal manual input, wherein the reviewer can mark (e.g., place a graphical object on) a portion of the detected observation (e.g., mark the region of interest (ROI)) and wherein the auto-contouring tool can estimate the remaining geometry of the observation based on the marked portion and image features associated with the marked portion. For example, the marked portion can include a line across the diameter of a detected observation, a circle or box placed imperfectly (loosely) around the detected observation, or the like. Additionally, or alternatively, the auto-contouring tool can allow the reviewer to more precisely outline the shape of the detected observation.

In either of these implementations, based on reception of user input applying some form of graphical mark-up identifying a location, size, and/or shape of a detected observation in at least one image, the lesion detection component 118 can segment the detected observation from the image. The lesion detection component 118 can also identify and segment the detected observation from other images included in the exam. The lesions detection component 118 can also determine the size (e.g., diameter) of detected lesions and potential lesions based on the received user mark-up input.

The feature detection component 120 can employ one or more feature detection algorithms to detect and characterize defined imaging features associated with a detected liver observation (e.g., a detected lesion or potential lesion) included in the liver exam image data 106. For example, these feature detection algorithms can be configured to evaluate the portions of the image data associated with the detected/segmented observation and determine information regarding (but not limited to) APHE, washout appearance, enhancing capsule appearance, observation size, and threshold growth. In various embodiments, the feature detection component 120 can employ separate feature detection algorithms for each defined imaging feature. In some embodiments, these feature detection algorithms can be configured to infer whether one or more of these features are present or absent in the observation. In other embodiments, the feature detection algorithms can be configured to infer a quantitative and/or qualitative measurable values for one or more of features.

For example, the feature detection algorithms can characterize the imaging features based on analysis of visual features associated with the observation itself and the observation relative to background visual features. These visual features can include for example, patterns in the image data related to enhancement (e.g., enhancement pattern information), morphological features and texture information. In some embodiments, the feature detection component 120 can characterize the imaging features (e.g., determine presence/absence, quantity, etc.) based on the number of voxels for each sub-component in the observation and one or more defined metrics. In some embodiments, the one or more defined metrics can relate to the relative enhancement of the observation's sub-components in comparison with adjacent liver parenchyma (referred to herein as the relative enhancement value and denoted as $\Delta HU$). The one or more defined metrics can also be based on noise-related information associated with the voxels (referred to herein as noise-related information and denoted as $\sigma N$). For example, the noise-related metric may include the level of noise in the adjacent liver parenchyma.

In some implementations, the feature detection component 120 can determine whether a feature is present or absent based on whether a measurable value for the feature (e.g., its $\Delta HU$ value, its $\sigma N$ value, or another measurable feature value) is above or below a threshold value. The feature detection component 120 can also determine whether the feature is present or absent if the algorithm confidence level is above a defined threshold confidence value. With these embodiments, the feature detection algorithms can be adapted to not only output a determination of whether a feature is present or absent, but a measure of confidence in the algorithm output (e.g., a measure of confidence in the determination that the feature is present or absent). In some implementations of these embodiments, the reporting component 124 can generate a warning notification in response to an inability of the feature detection component 120 to accurately determine whether a feature is present or absent based on the associated confidence value. For example, if the confidence value is low (e.g., outside a threshold value or range), the reporting component 124 can generate a warning notification that can be presented to the reviewer via the medical imaging application (e.g., via the rendering component 112 and/or the reporting component 124). The warning notification can prompt the reviewer to manually review and characterize presence or absence of the feature and/or manually evaluate the pathology of lesion/potential lesion.

The feature value and confidence thresholds can vary depending on the phase and the feature. For example, the feature detection component 120 can determine whether non-rime APHE is present or absent based on the $\Delta HU$ value and the $\sigma N$ value determined for the observation in images in the arterial phase. In another example, the feature detection component 120 can determine whether washout and capsule features are present or absent based on the $\Delta HU$ value and the $\sigma N$ value determined for the observation in images in the portal venous phase and the delayed phase. The thresholds for these metrics can vary based on the phase. It should be appreciated that relative enhancement ($\Delta HU$) and noise-related information ($\sigma N$) are merely some example metrics for evaluating and detecting/characterizing liver features in medical image data and various other metrics may also be used.

FIG. 2 provides a table (Table 200) defining some example feature detection metrics that can be used to detect and characterize imaging features in accordance with one or more embodiments of the disclosed subject matter. Table 200 provides example feature detection metrics for evaluating presence or absence of the non-rim APHE, washout, and capsules based on $\Delta HU$ and $\sigma N$. As illustrated in table 200, certain feature values are not applicable in certain phases. For example, in accordance with Table 200, the feature detection component 120 can determine that washout is present in the portal venous phase if $\Delta HU=(-)$ 12.2 and $\sigma N=(\pm)$ 13.2, and determine that washout is present in the delayed phase if $\Delta HU=(-)$ 8.4 and $\sigma N=(\pm)$ 13.2. In another example, the feature detection component 120 can determine that capsule is present in the portal venous phase if $\Delta HU=(+)$ 3.0 and $\sigma N=(\pm)$ 13.2, and determine that capsule is present in the delayed phase if $\Delta HU=(+)$ 4.0 and $\sigma N=(\pm)$ 13.2.

With reference again to FIG. 1, the scoring component 122 can facilitate evaluating the pathology of a detected observation. In various embodiments, the scoring component 122 can apply one or more diagnostic/scoring algorithms that can classify or score the pathology of an observation with a value representative of whether and to what degree the observation is HCC based at least in part on the results of the one or more feature detection algorithms. For example, the one or more diagnostic/scoring algorithms can generate an HCC score for a detected observation based on the relative enhancement ($\Delta HU$) and the noise-related information ($\sigma N$) determined for the applicable features (e.g., APHE, washout, and capsule) in the applicable phases. The scoring component can also take into consideration the detected capsule size, location and geometry, and threshold growth when scoring the observation. In some embodiments, the one or more diagnostic algorithms can apply the LI-RADS® ontology in association with evaluating and scoring liver observations. The LI-RADS protocol categorizes observations on a spectrum from definitely benign to definitely HCC.

The reporting component 124 can generate a diagnostic report summarizing the results of the lesion detection component 118, the feature detection component 120 and the scoring component 122. In the embodiment shown, the reported information is identified as liver assessment data 130. For example, the liver assessment data 130 can include but is not limited to: information identifying the number of observations detected, information identifying the size, location and geometry of the observations detected, information regarding the imaging features detected and their corresponding metrics, and the determined HCC score for the respective observations. The liver assessment data 130 can be presented via the user device 134, stored in one or more medical data sources, and/or exported to another device or system for initiating responsive actions based on the results in the report. The assessment tools component 125 can further provides one or more assessment tools (e.g., the phase identification tool 308, the observation evaluation tool 310 and other tools described infra) via the graphical user interface of the medical imaging application that facilitate manually reviewing and receiving user input in association with generating the assessment report in accordance with a guided workflow. For example, these assessment tools can include interactive tools for manually reviewing and editing the information automatically generated by the phase identification component 114, the lesion detection component 118, the feature detection component 120 and the scoring component 122. These interactive assessment tools are further described in association with reference to FIGS. 4-9.

In this regard, FIGS. 4-9 provide additional example graphical user interfaces that provided by the medical imaging application discussed with reference to FIG. 3. These additional graphical user interfaces demonstrate some of the features and functionalities of the lesion detection component 118, the feature detection component 120, the scoring component 122, the assessment tools component 125 and reporting component 124 in association with integration with the medical imaging application. Repetitive description of like elements employed in respective embodiments is omitted for sake of brevity.

Figure 4:
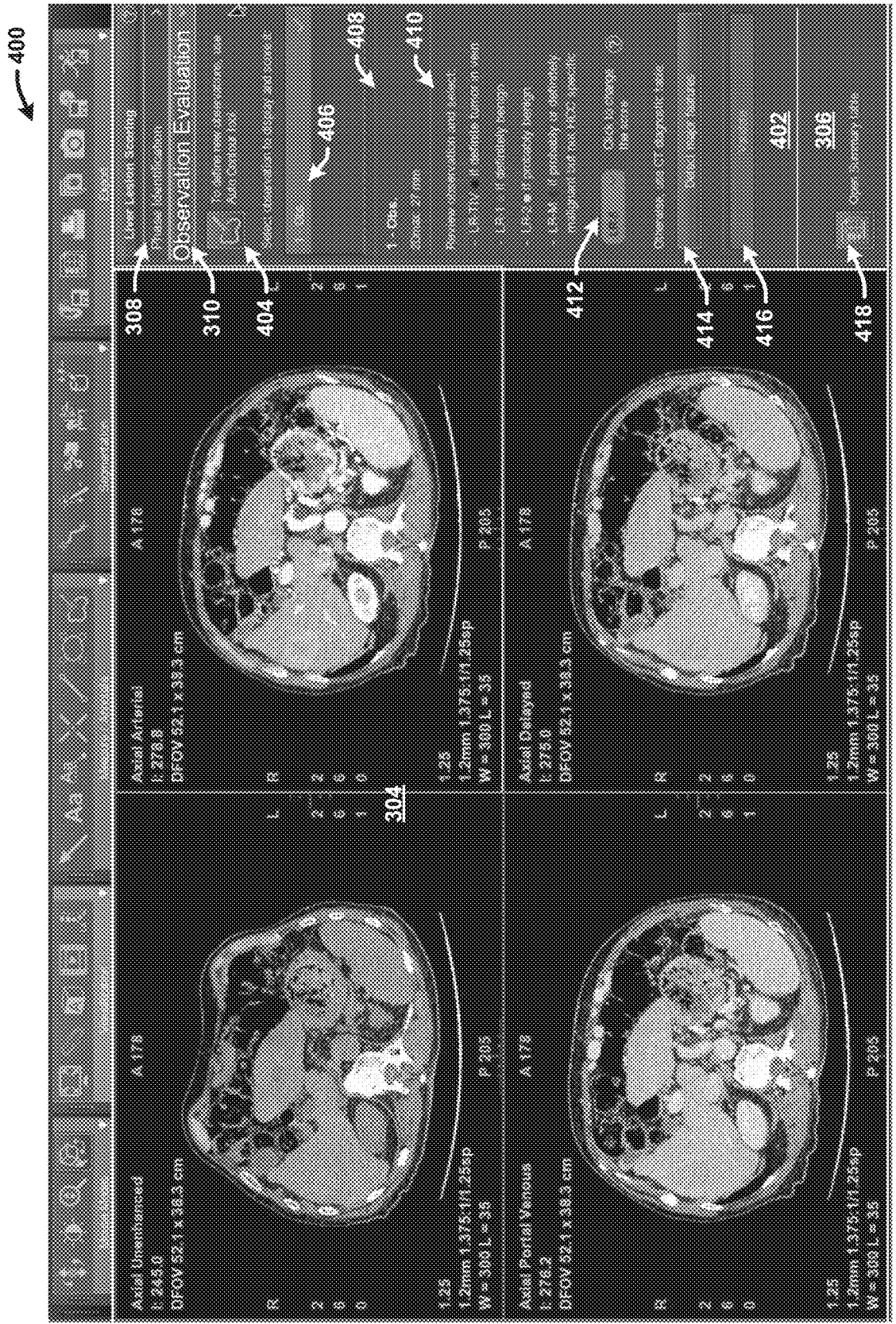

FIG. 4 presents an example graphical user interface 400 illustrating some features and functionalities of the observation evaluation tool 310. In the embodiment shown, the observation evaluation tool 310 has been selected to generate an evaluation window 402 including various functions and information that facilitate defining and evaluating observations included in the displayed images. These functions include an observation defining function 410, a scoring function 412, a feature detection function 414 and a validation function 416.

The observation defining function 410 can provide for manually marking an observation depicted in a displayed image. Additionally, or alternatively, the observations can be automatically identified and segmented by the lesion detection component 118 using one or more lesion detection algorithms as discussed above. Once an observation has been identified and defined, it can be assigned an identifier (e.g., observation 1, or 1-Obs.) and displayed below the observation defining tool 404. Information regarding the observation's size (e.g., diameter) and shape (e.g., volume) can further be determined/extracted by the lesion detection component 118 and displayed below the observation defining function 410.

Figure 5:
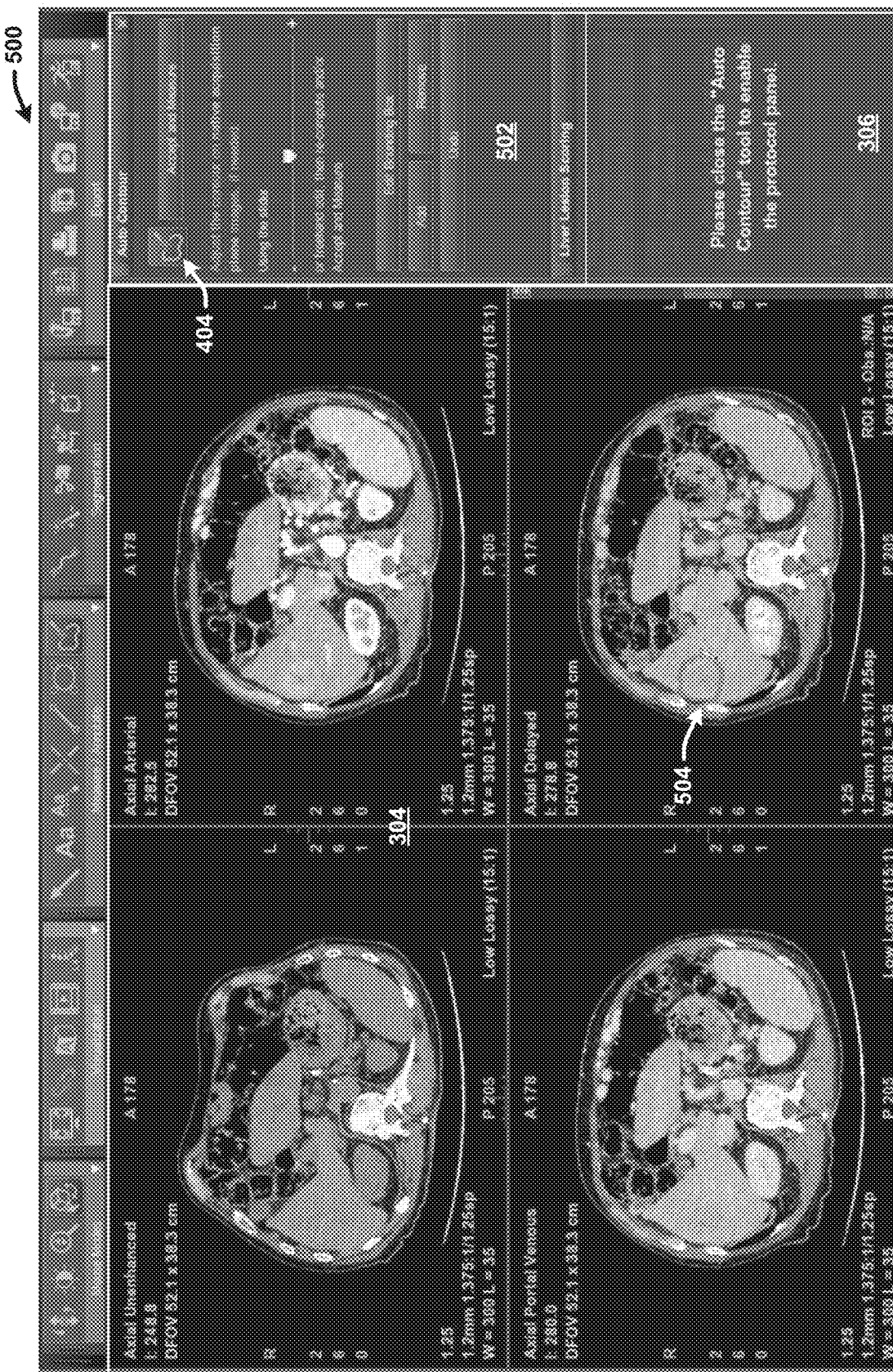

FIG. 5 presents an example graphical user interface 500 demonstrating some features and functionalities of the observation defining function 404. In the embodiment shown, the observation defining function 404 has been selected to reveal mark-up and contouring tools associated therewith that can be used to manually mark and define an observation in a displayed image. These tools are respectively included in a new observation defining window 502. In some embodiments, these tools can provide for editing the bounding box of an auto-detected and segmented lesion (e.g., as generated by the lesion detection component 118 using one or more lesion segmentation models). Additionally, or alternatively, these tools can allow a user to free-handedly mark lesion with a bounding box, a diameter mark up or the like. These tools can also allow the user to adjust the contour on native acquisition image planes if needed using a slider widget. In the embodiment shown, a bounding box 504 has been manually applied to a detected lesion using these contouring tools. Once the diameter and/or outline boundary of a lesion has been defined relative to the image, the lesion detection component 118 can compute its actual diameter and volume.

With reference again to FIG. 4, the scoring function 412 provides for scoring an identified observation with an HCC score. In the embodiment shown, the scoring function 412 provide a drop-down menu with selectable HCCs scores that can be manually selected and applied to a selected observation, which in this example is observation labeled 1-Obs. The LI-RADS® scoring system is used in this example implementation and a LI-RADS score of LR-5 has been applied to Obs. 1. The evaluation window further provides reference scoring information 410 that can be used by the reviewer to guide their determination regarding the appropriate score for an observation. In some embodiments, the system can automatically apply an estimated HCC score to a detected observation using one or more diagnostic/scoring algorithms as discussed above. The scoring function 412 can further allow the user to manually adjust/edit the auto-generated score as deemed appropriate.

The feature detection function 414 can provide for detecting and characterizing imaging features associated with (or not associated with) a selected observation. For example, in various embodiments, selection of the feature detection function can cause the feature detection component 120 to process the image data using the one or more feature detection algorithms and generate corresponding results which can be displayed and reviewed in the graphical user interface and used by the scoring component to generate the HCC score for the observation.

Figure 6:
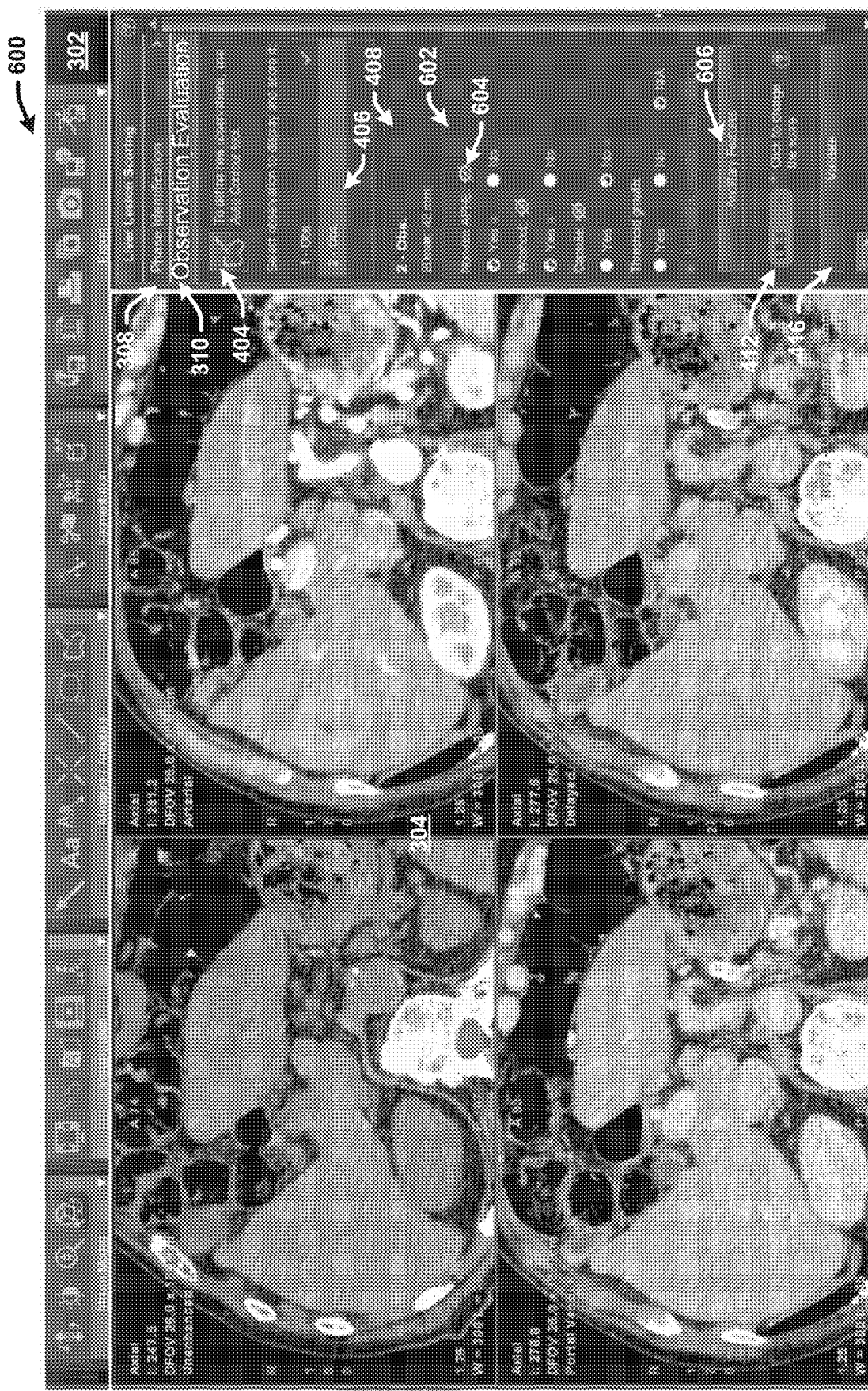

FIG. 6 provides an example graphical user interface 600 that can be generated in response to selection of the feature detection function 414. Information regarding the imaging features is displayed in a new imaging feature area 602 of the display. In this example, the imaging features evaluated/detected by the feature detection component 120 include non-rim APHE, washout, capsule and threshold growth. Features that are considered detected are marked "yes" while features that are not detected are marked "no". The imaging features evaluated can further be selected using the 'eye' icon associated therewith to view the specific images where the features were detected for the observation.

Figure 7:
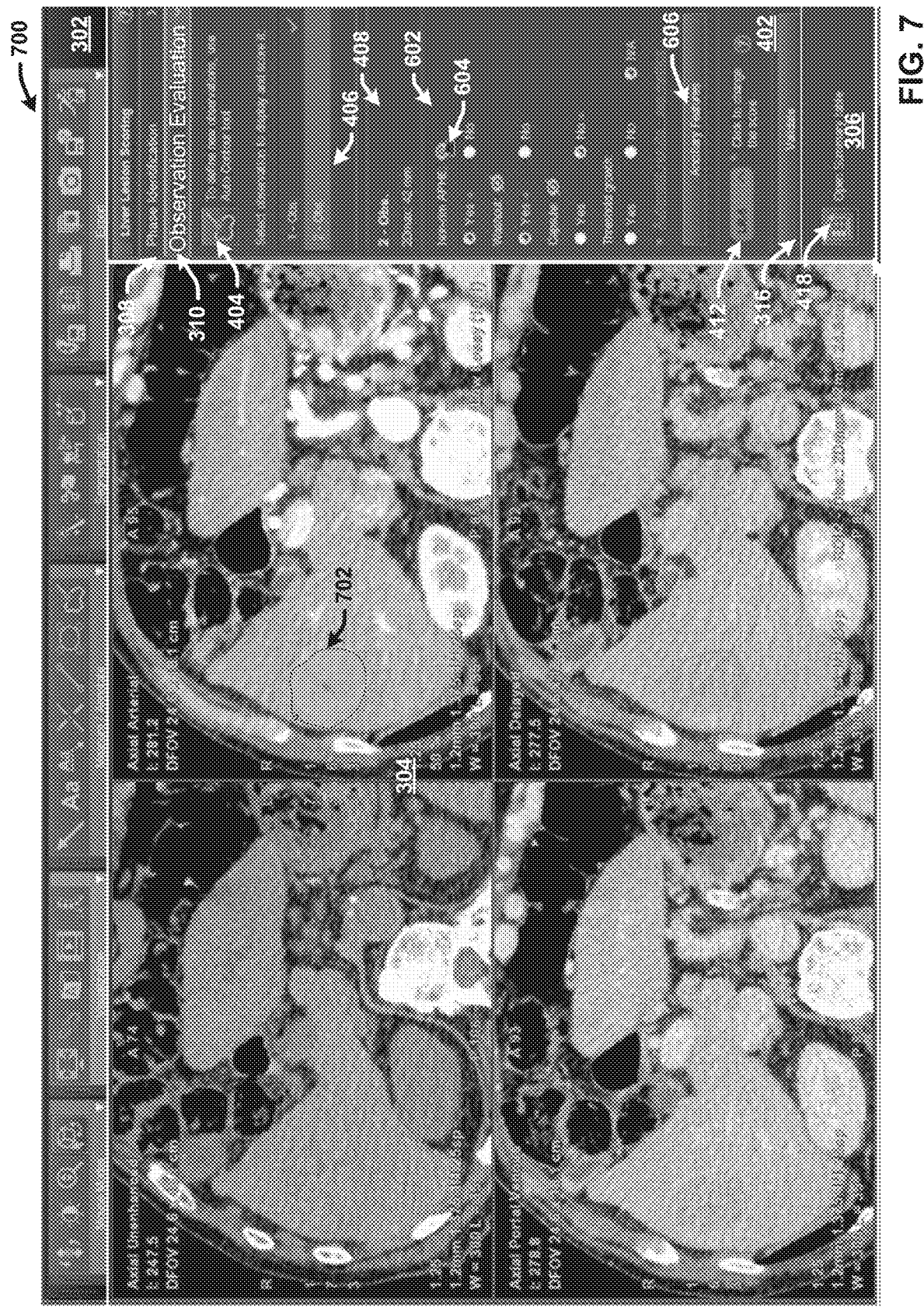

For example, FIG. 7 provides an example user interface 700 that can be generated in response to selection of eye icon 604 for the non-rim APHE feature. As shown in FIG. 7, the non-rim APHE feature was detected for an observation as it appears in the arterial phase. The feature detection function 414 can further visually indicate (e.g., with highlighting, with a bounding box, etc.) the observation 702 with the detected feature directly on the image data.

Figure 8:

The feature detection function 414 further include an ancillary features function 606 that provide for annotating a selected observation with ancillary features. For example, FIG. 8 provides an example graphical user interface 800 that can be generated in response to selection of the ancillary features function. As shown in FIG. 8, the ancillary features function 606 can provide the user with a dialog-box of with a list ancillary features that can be selectively applied to a particular observation. These ancillary features include pre-defined ancillary features favoring malignancy in general (not HCC in particular), ancillary features favoring malignancy for HCC in particular, and ancillary features favoring benignity.

With reference again to FIG. 4, the validation function 416 can be selected by a reviewer upon completion of their evaluation of the liver image data to confirm and validate the information generated/collected therefrom. For example, once the reviewer has finished identifying and scoring all lesions and potential lesions and applying ancillary features, they can select the validation function 416 to complete their review and provide their stamp of approval.

Figure 9:
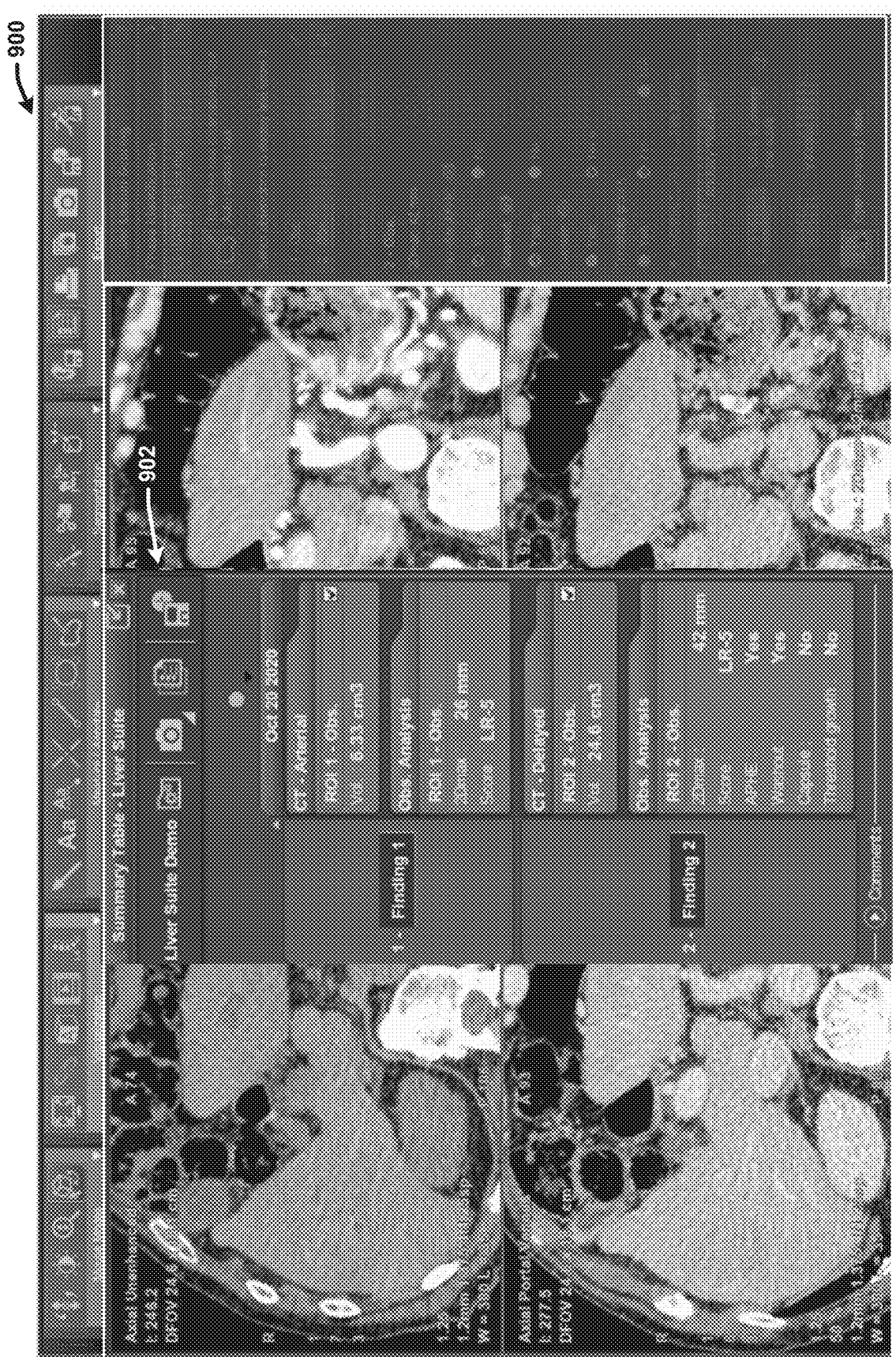

The right-side panel further includes a summary table icon 418 that can be selected to review a summary of observation evaluation generated using the observation evaluation tool 310, as shown in FIG. 9. In this regard, FIG. 9 presents another graphical user interface 900 illustrating an example summary table 902 that can be generated in response to selection of the summary table icon 416. In various embodiments, the summary table 902 can be generated by the reporting component 124 and save, exported, associated with the patient's record and the like. Each detected observation can be reported as finding, which in this example includes two. The summary table 902 can include information identifying the observations detected, the particular image series where it was detected, its size (e.g., diameter, volume, etc.), its HCC score (which in this example includes a LI-RADS® score), and the imaging features detected.

As illustrated in FIGS. 3-9, the disclosed techniques provide an integrated environment for the review and analysis of liver images, with guided workflows and tools to support clinical decisions on liver cancer classification according to standardized guidelines and ontologies. These tools can significantly aid physicians in applying accurate and structured clinical reports regarding liver cancer exams and to improve communication with referring physicians in association with making more informed and appropriate patient management decisions.

Figure 10:
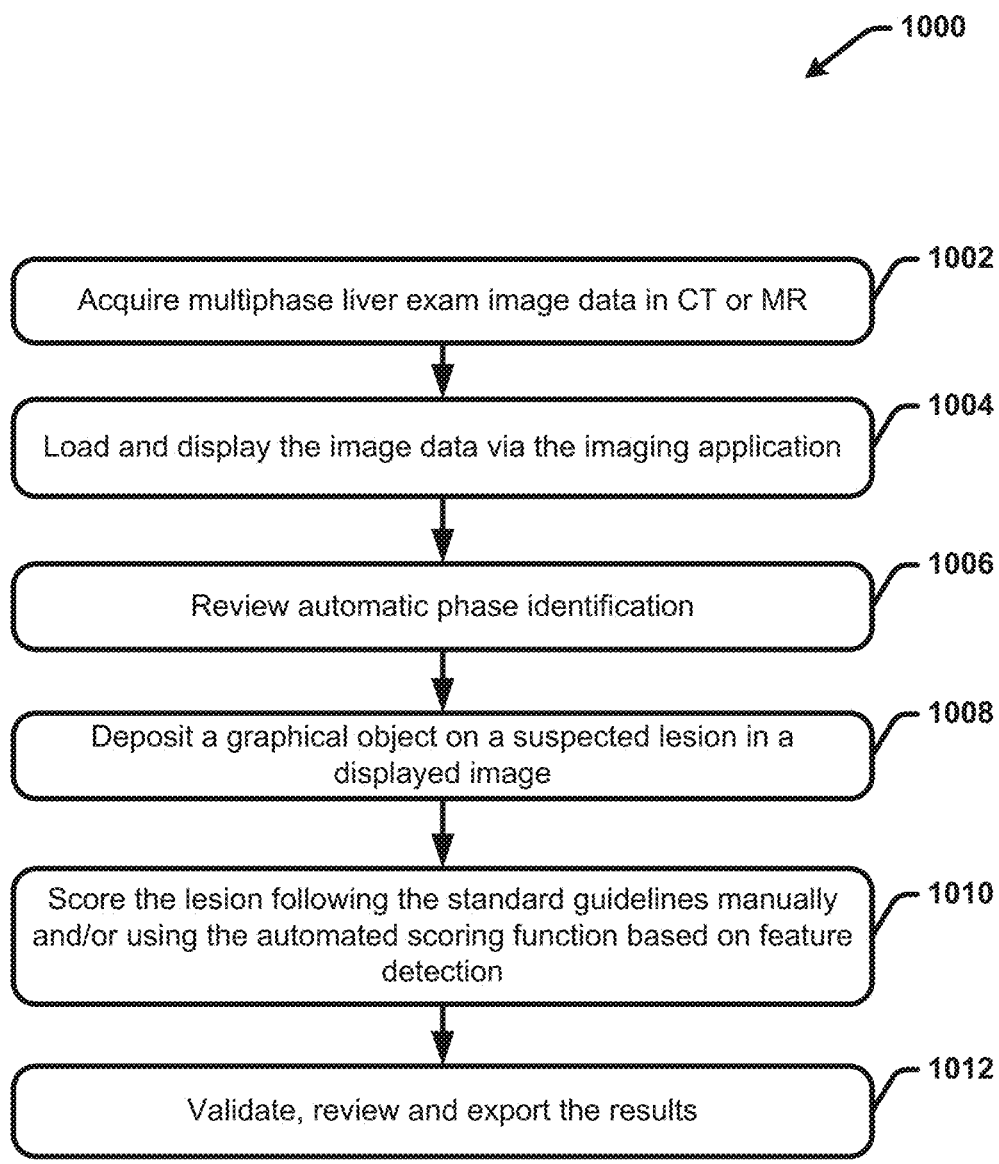
FIG. 10 provides a flow diagram of an example workflow for evaluating liver imaging exams in accordance with one or more embodiments of the disclosed subject matter.

FIG. 10 provides a flow diagram of an example workflow 1000 for evaluating liver imaging exams using system 100 and a medical imaging application integrating the features and functionalities of the liver assessment module 110. Workflow 1000 demonstrates various steps that can be performed from a user's perspective (e.g., a radiologist, a clinician, a technician, etc.). Repetitive description of like elements employed in respective embodiments is omitted for sake of brevity.

With reference to FIGS. 1 and 10, in accordance with method 1000, at 1002 multiphase liver exam data can be acquired in CT or MR. For example, the multiphase liver exam data (e.g., multiphase liver exam data 106) can be acquired directly from the imaging device 102 and/or from one or more medical data sources 104. At 1004, the image data can be loaded and displayed via the imaging application in association with access and usage of the imaging application at the user device 134. At 1006, the user can review the automatic phase identification performed by the phase identification component 114 (e.g., as described with reference to FIG. 3). At 1008, the user can deposit a graphical object on a suspect lesion in a displayed image (e.g., as described with reference to FIGS. 4 and 5). At 1010, the lesion can be scored following the standard guidelines (e.g., LI-RADS® or the like), either manually and/or using the automated lesion scoring function based on feature detection (e.g., as described with reference to FIGS. 4 and 6). At 1012, the results can be validated, reviewed and exported, as described with reference to FIGS. 4 and 9.

Figure 11:
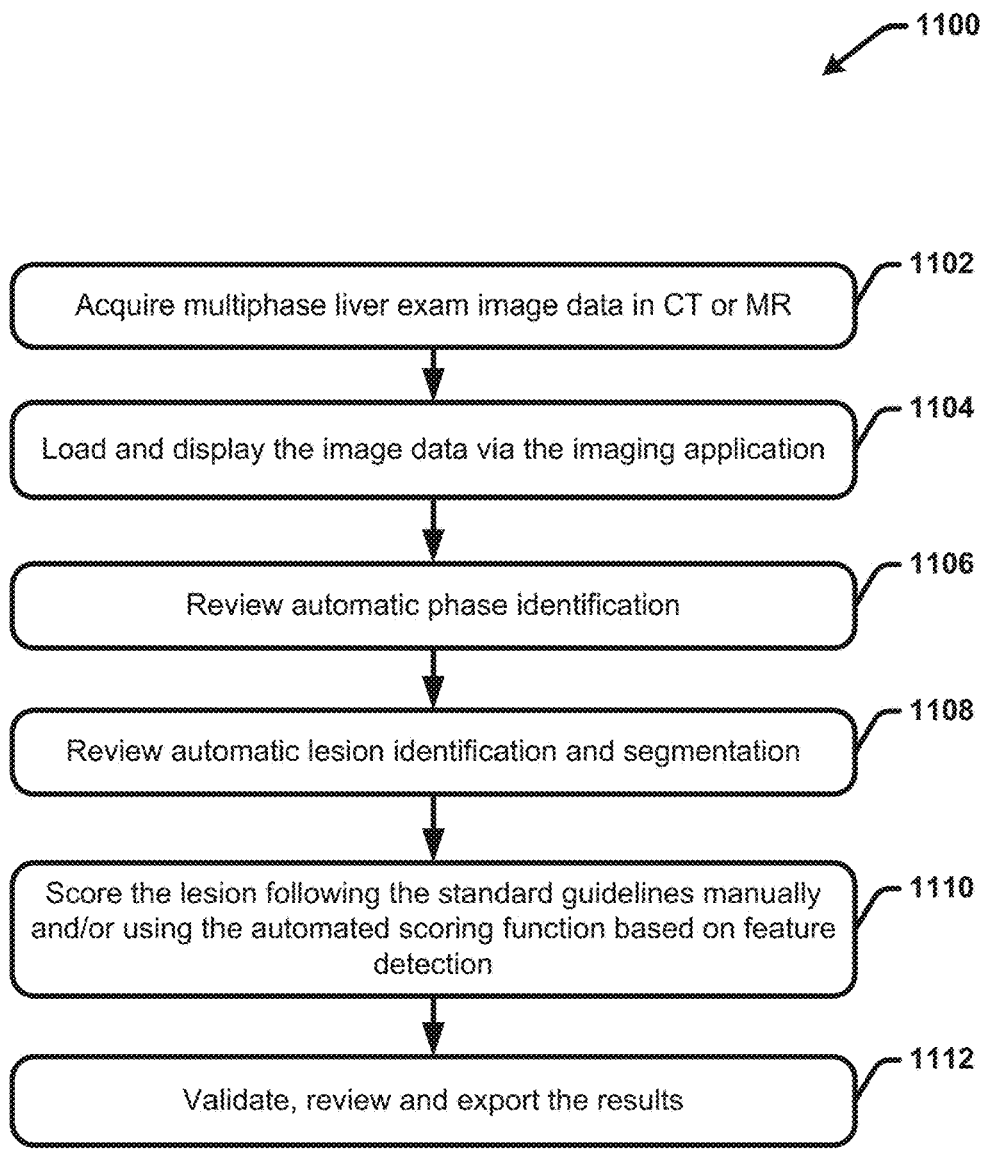
FIG. 11 provides a flow diagram of an example workflow for evaluating liver imaging exams in accordance with one or more embodiments of the disclosed subject matter.

FIG. 11 provides a flow diagram of another example workflow 1100 for evaluating liver imaging exams using system 100 and a medical imaging application integrating the features and functionalities of the liver assessment module 110. Workflow 1000 demonstrates various steps that can be performed from a user's perspective (e.g., a radiologist, a clinician, a technician, etc.). Repetitive description of like elements employed in respective embodiments is omitted for sake of brevity.

With reference to FIGS. 1 and 11, in accordance with method 1100, at 1002 multiphase liver exam data can be acquired in CT or MR. For example, the multiphase liver exam data (e.g., multiphase liver exam data 106) can be acquired directly from the imaging device 102 and/or from one or more medical data sources 104. At 1104, the image data can be loaded and displayed via the imaging application in association with access and usage of the imaging application at the user device 134. At 1108, the user can review the automatic lesion identification performed by the lesion identification component 118 using one or more lesion segmentation models. At 1108, the user can deposit a graphical object on a suspect lesion in a displayed image (e.g., as described with reference to FIGS. 4 and 5). At 1110, the lesion can be scored following the standard guidelines (e.g., LI-RADS® or the like), either manually and/or using the automated lesion scoring function based on feature detection (e.g., as described with reference to FIGS. 4 and 6). At 1012, the results can be validated, reviewed and exported, as described with reference to FIGS. 4 and 9.

Figure 12:
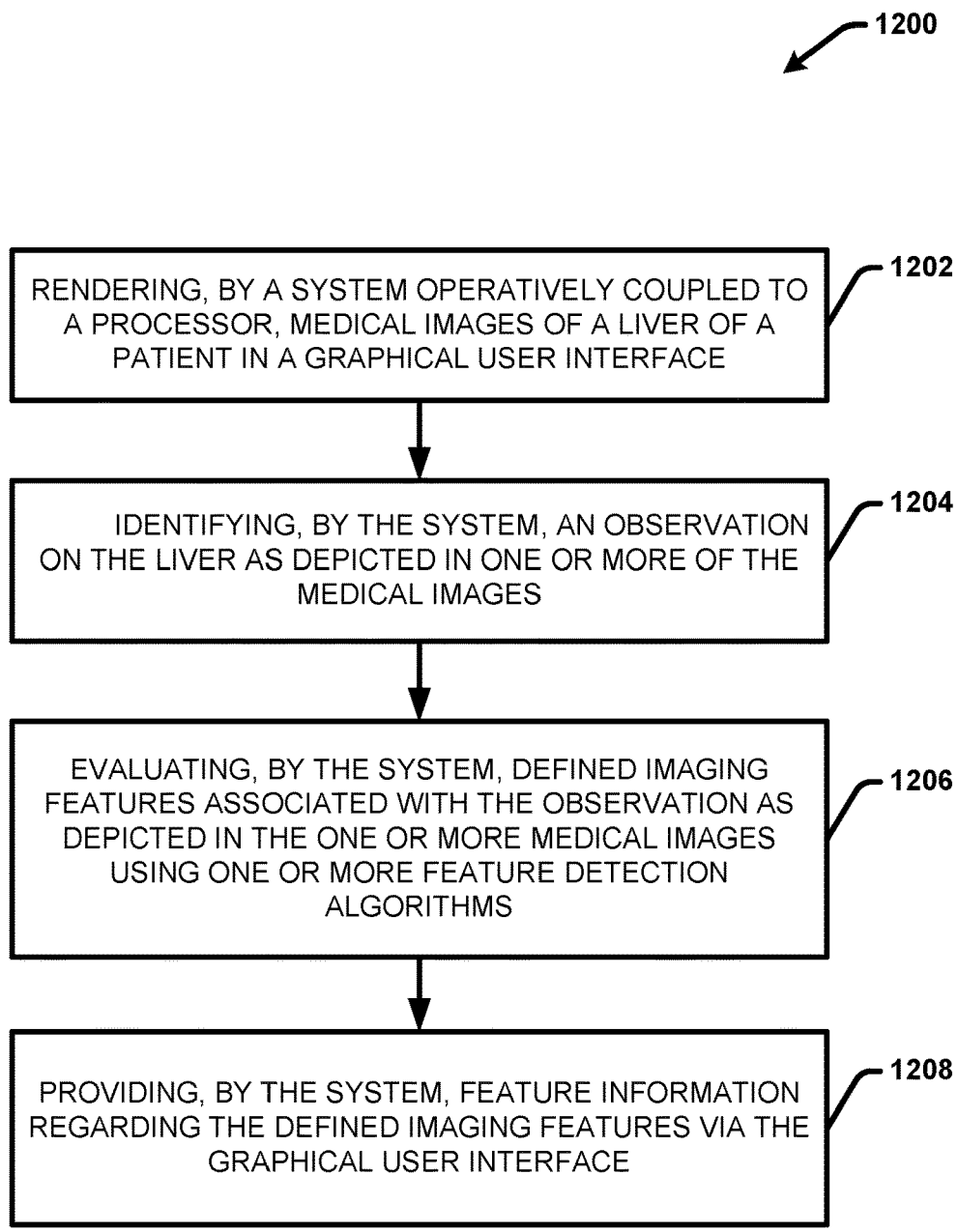
FIG. 12 presents a high-level flow diagram of an example computer-implemented process for evaluating liver imaging exams and observations features using AI analytics in accordance with one or more embodiments of the disclosed subject matter.

FIG. 12 presents a high-level flow diagram of an example computer-implemented process 1200 for evaluating liver imaging exams and observations features using AI analytics in accordance with one or more embodiments of the disclosed subject matter. Repetitive description of like elements employed in respective embodiments is omitted for sake of brevity.

At 1202, a system operatively coupled to a processor (e.g., system 100) can render medical images of a liver of a patient in a graphical user interface (e.g., using rendering component 112). At 1204, the system can identify an observation on the liver as depicted in one or more of the medical images (e.g., using lesion detection component 118). At 1206, the system can evaluate defined imaging features associated with the observation as depicted in the one or more medical images using one or more feature detection algorithms (e.g., via the feature detection component 120). At 1208, the system can provide feature information regarding the defined imaging features via the graphical user interface (e.g., via reporting component 124 and rendering component 112).

Figure 13:
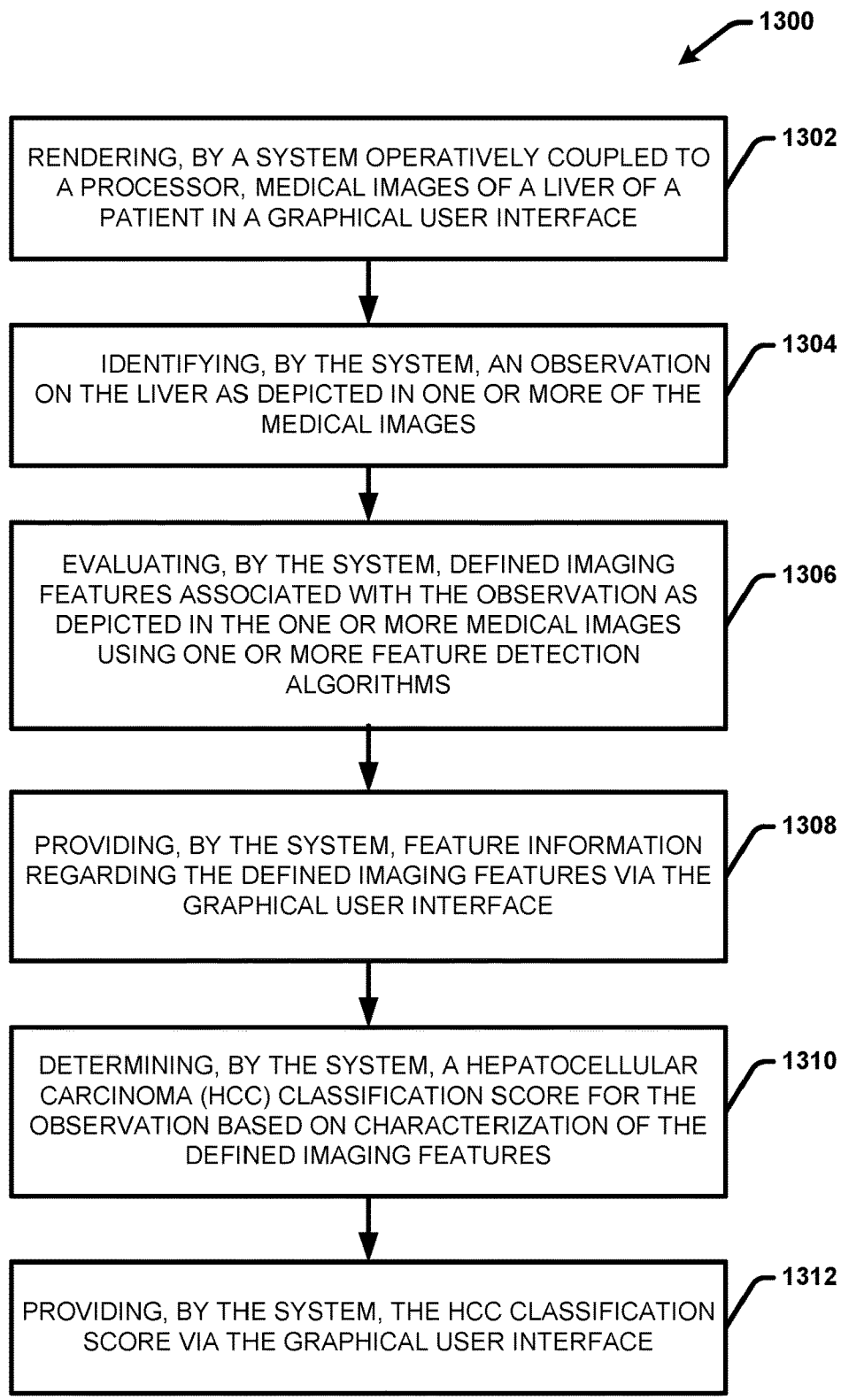
FIG. 13 presents a high-level flow diagram of an example computer-implemented process for evaluating liver imaging exams and diagnosing liver cancer using AI analytics in accordance with one or more embodiments of the disclosed subject matter.

FIG. 13 presents a high-level flow diagram of an example computer-implemented process 1000 for evaluating liver imaging exams and diagnosing liver cancer using AI analytics in accordance with one or more embodiments of the disclosed subject matter. Repetitive description of like elements employed in respective embodiments is omitted for sake of brevity.

At 1302, a system operatively coupled to a processor (e.g., system 100) can render medical images of a liver of a patient in a graphical user interface (e.g., using rendering component 112). At 1304, the system can identify an observation on the liver as depicted in one or more of the medical images (e.g., using lesion detection component 118). At 1306, the system can evaluate defined imaging features associated with the observation as depicted in the one or more medical images using one or more feature detection algorithms (e.g., via the feature detection component 120). At 1308, the system can provide feature information regarding the defined imaging features via the graphical user interface (e.g., via reporting component 124 and rendering component 112). At 1310, the system can determine a HCC classification score for the observation based on characterization of the defined imaging features (e.g., using scoring component 122). At 1312, the system can provide the HCC classification score via the graphical user interface (e.g., via reporting component 124 and rendering component 112).

Example Operating Environment

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 14, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 14:
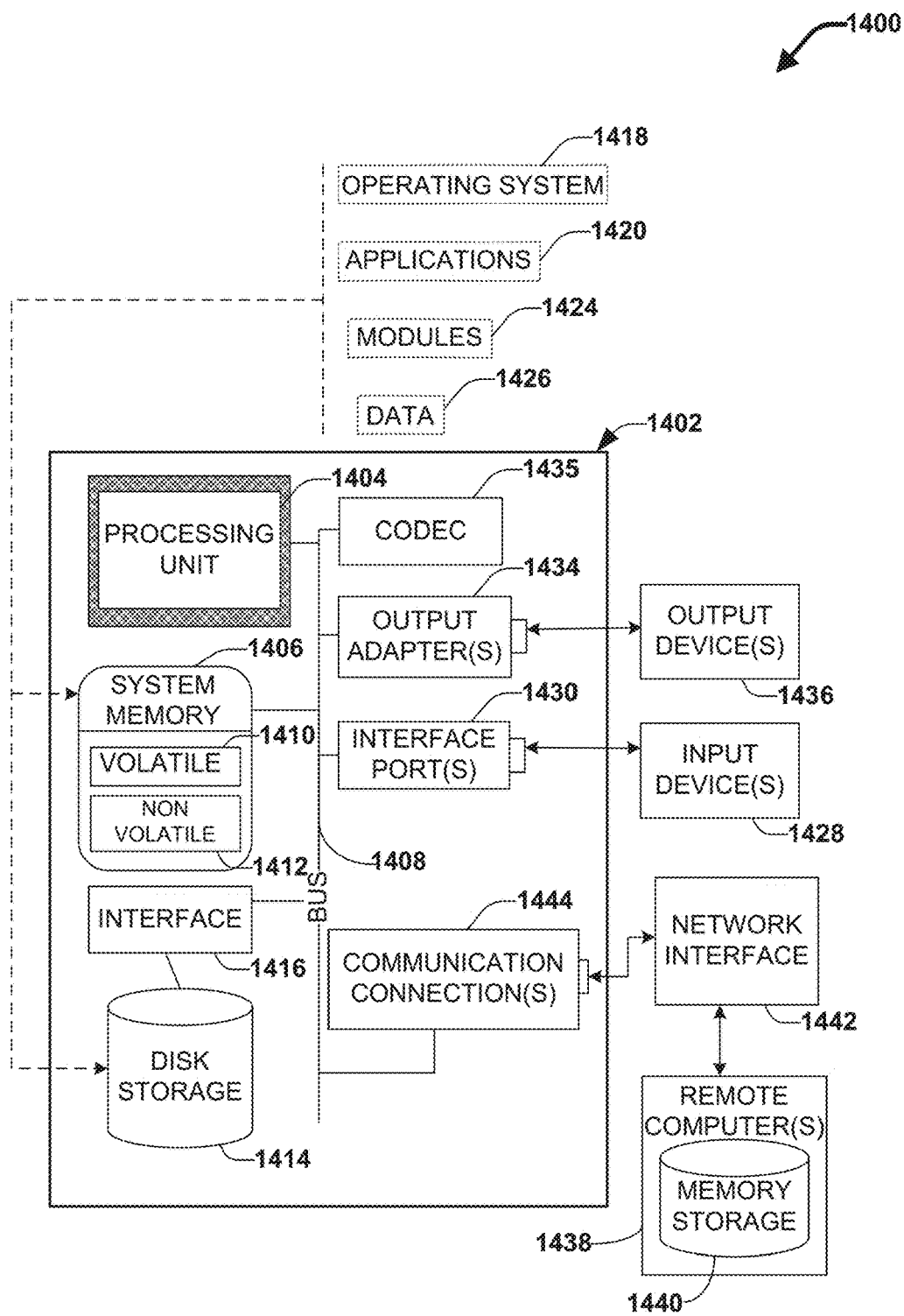
FIG. 14 illustrates a block diagram of an example, non-limiting operating environment in which one or more embodiments described herein can be facilitated.

With reference to FIG. 14, an example environment 1400 for implementing various aspects of the claimed subject matter includes a computer 1402. The computer 1402 includes a processing unit 1404, a system memory 1406, a codec 1435, and a system bus 1408. The system bus 1408 couples system components including, but not limited to, the system memory 1406 to the processing unit 1404. The processing unit 1404 can be any of various available processors. Dual microprocessors and other multiprocessor architectures also can be employed as the processing unit 1404.

The system bus 1408 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1406 includes volatile memory 1410 and non-volatile memory 1412, which can employ one or more of the disclosed memory architectures, in various embodiments. The basic input/output system (BIOS), containing the basic routines to transfer information between elements within the computer 1402, such as during start-up, is stored in non-volatile memory 1412. In addition, according to present innovations, codec 1435 can include at least one of an encoder or decoder, wherein the at least one of an encoder or decoder can consist of hardware, software, or a combination of hardware and software. Although, codec 1435 is depicted as a separate component, codec 1435 can be contained within non-volatile memory 1412. By way of illustration, and not limitation, non-volatile memory 1412 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1412 can employ one or more of the disclosed memory devices, in at least some embodiments. Moreover, non-volatile memory 1412 can be computer memory (e.g., physically integrated with computer 1402 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1410 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1402 can also include removable/non-removable, volatile/non-volatile computer storage medium. FIG. 14 illustrates, for example, disk storage 1414. Disk storage 1414 includes, but is not limited to, devices like a magnetic disk drive, solid state disk (SSD), flash memory card, or memory stick. In addition, disk storage 1414 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1414 to the system bus 1408, a removable or non-removable interface is typically used, such as interface 1416. It is appreciated that disk storage 1414 can store information related to a user. Such information might be stored at or provided to a server or to an application running on a user device. In one embodiment, the user can be notified (e.g., by way of output device(s) 1436) of the types of information that are stored to disk storage 1414 or transmitted to the server or application. The user can be provided the opportunity to opt-in or opt-out of having such information collected or shared with the server or application (e.g., by way of input from input device(s) 1428).

It is to be appreciated that FIG. 14 describes software that acts as an intermediary between users and the basic computer resources described in the suitable operating environment 1400. Such software includes an operating system 1418. Operating system 1418, which can be stored on disk storage 1414, acts to control and allocate resources of the computer 1402. Applications 1420 take advantage of the management of resources by operating system 1418 through program modules 1424, and program data 1426, such as the boot/shutdown transaction table and the like, stored either in system memory 1406 or on disk storage 1414. It is to be appreciated that the claimed subject matter can be implemented with various operating systems or combinations of operating systems.

A user enters commands or information into the computer 1402 through input device(s) 1428. Input devices 1428 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1404 through the system bus 1408 via interface port(s) 1430. Interface port(s) 1430 include, for example, a serial port, a parallel port, a game port, and a universal serial bus (USB). Output device(s) 1436 use some of the same type of ports as input device(s) 1428. Thus, for example, a USB port can be used to provide input to computer 1402 and to output information from computer 1402 to an output device 1436. Output adapter 1434 is provided to illustrate that there are some output devices 1436 like monitors, speakers, and printers, among other output devices 1436, which require special adapters. The output adapters 1434 include, by way of illustration and not limitation, video and sound cards that provide a means of connection between the output device 1436 and the system bus 1408. It should be noted that other devices or systems of devices provide both input and output capabilities such as remote computer(s) 1438.

Computer 1402 can operate in a networked environment using logical connections to one or more remote computers, such as remote computer(s) 1438. The remote computer(s) 1438 can be a personal computer, a server, a router, a network PC, a workstation, a microprocessor based appliance, a peer device, a smart phone, a tablet, or other network node, and typically includes many of the elements described relative to computer 1402. For purposes of brevity, only a memory storage device 1440 is illustrated with remote computer(s) 1438. Remote computer(s) 1438 is logically connected to computer 1402 through a network interface 1442 and then connected via communication connection(s) 1444. Network interface 1442 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1444 refers to the hardware/software employed to connect the network interface 1442 to the bus 1408. While communication connection 1444 is shown for illustrative clarity inside computer 1402, it can also be external to computer 1402. The hardware/software necessary for connection to the network interface 1442 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," "data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
 a memory that stores computer executable components; and
 a processor that executes the computer executable components stored in the memory, wherein the computer executable components comprise:
  a rendering component that facilitates rendering medical images of a liver of a patient in a graphical user interface of a medical imaging application that facilitates evaluating the medical images, wherein the rendering component associates different groups of the medical images in different windows of the graphical user interface, the different groups corresponding to different hepatic vascular phases;
  a lesion detection component that identifies an observation on the liver as depicted in at least some of the medical images; and
  a feature detection component that determines, based on application of one or more feature detection algorithms to the at least some of the medical images, whether each feature included in a defined set of features, is present or absent for the observation, wherein the one or more feature detection algorithms are configured to detect each feature in a subset of the different groups,
  wherein the rendering component renders results of the feature detection component via the graphical user interface, wherein the results indicate whether each feature is present or absent for the observation, and
  wherein based on a feature being indicated as present, the results comprise an interactive view button associated with the feature which in response to selection thereof, causes the rendering component to render a representative image of the at least some of the medical images comprising the feature in a window of the different windows corresponding to a group of the different groups to which the representative image belongs.

2. The system of claim 1, wherein the computer executable components further comprise:
 a scoring component that determines a hepatocellular carcinoma (HCC) classification score for the observation based on the results of the feature detection component, wherein the rendering component further renders the HCC classification score via the graphical user interface.

3. The system of claim 2, wherein the computer executable components further comprise:
 a reporting component that generates an assessment report of health of the liver based on the observation, the HCC classification score and the results of the feature detection component; and
 an assessment tools component that provides one or more assessment tools via the graphical user interface that facilitate manually reviewing and receiving user input in association with generating the assessment report in accordance with a guided workflow.

4. The system of claim 3, wherein the one or more assessment tools comprise an ancillary features function that provides an interactive list of ancillary features via the graphical user interface that can be selectively applied to the observation via manual input and included in the assessment report.

5. The system of claim 1, wherein the defined set of features comprises an arterial phase hyperenhancement feature, a washout appearance feature, and an enhancing capsule appearance feature.

6. The system of claim 1, wherein the one or more feature detection algorithms determine presence of absence of each feature for the observation based on analysis of one or more of, enhancement pattern information, morphological information and texture information associated with the observation.

7. The system of claim 1, wherein the feature detection component determines presence or absence of each feature for the observation based on confidence scores associated with the outputs generated by the one or more feature detection algorithms.

8. The system of claim 7, wherein the computer executable components further comprise:
 a reporting component that generates a warning notification in response to an inability of the feature detection component to accurately detect presence of absence of a feature based on a confidence score associated with the feature being outside a defined confidence region, and wherein the rendering component provides the warning notification via the graphical user interface in association with visual and numerical assessment tools of the medical imaging application that facilitate manual assessment of the medical images.

9. The system of claim 1, wherein the computer executable components further comprise:
 a phase identification component that identifies and separates the medical images into the different groups based on application of one or more phase identification algorithms to the medical images.

10. The system of claim 9, wherein the graphical user interface comprises a phase identification tool that provides for editing, via manual input, respective phase type classifications of the medical images as determined by the phase identification component.

11. The system of claim 1, wherein the one or more feature detection algorithms determine, for each feature, a first measure of relative enhancement associated with the observation and a second measure of noise associated with the observation, and wherein the feature detection component determines whether each feature is present or absent for the observation based on whether the first measure and the second measure respectively exceed a relative enhancement measure threshold and a noise measure threshold.

12. The system of claim 11, wherein the relative enhancement measure threshold and the noise measure threshold vary for each feature of the defined set of features.

13. The system of claim 1, wherein in association rendering the representative medical image, the rendering component renders a visual indicator identifying a position of the observation as included in the representative medical image.

14. The system of claim 1, wherein in association with rendering the representative medical image, the rendering component renders mark-up data applied to the representative medical image that depicts the feature and provides information describing the feature, the information comprising one metrics used to characterize the feature.

15. A method comprising:
 facilitating rendering, by a system operatively coupled to a processor, medical images of a liver of a patient in a graphical user interface of a medical imaging application that facilitates evaluating the medical images, wherein the facilitating comprises associating different groups of the medical images in different windows of the graphical user interface, the different groups corresponding to different hepatic vascular phases;

identifying, by the system, an observation on the liver as depicted in at least some of the medical images;

determining, by the system based on application of one or more feature detection algorithms to the at least some of the medical images, whether each feature included in a defined set of features, is present or absent for the observation, wherein the one or more feature detection algorithms are configured to detect each feature in a subset of the different groups;

providing, by the system, feature information via the graphical user interface indicating whether each feature is present or absent for the observation, and wherein the feature information comprises, for a feature being indicated as present, an interactive view button associated with the feature;

identifying, by the system in response to selection of the interactive view button, a representative medical image of the at least some of the medical images comprising the feature; and rendering, by the system in response to selection of the interactive view button, the representative medical image included in the subset in a window of the different windows corresponding to a group of the different groups to which the representative image belongs.

16. The method of claim 15, further comprising:

determining, by the system, a hepatocellular carcinoma (HCC) classification score for the observation based on results of the one or more feature detection algorithms; and providing, by the system, the HCC classification score via the graphical user interface.

17. The method of claim 15, wherein the defined set of features comprises an arterial phase hyperenhancement feature, a washout appearance feature, and an enhancing capsule appearance feature.

18. The method of claim 15, wherein the evaluating comprises determining presence or absence of each feature for the observation based on confidence scores associated with the outputs generated by the one or more feature detection algorithms.

19. The method of claim 15, further comprising:

identifying, by the system, the different groups based on application of one or more phase identification algorithms to the medical images; and separating, by the system, the medical images into the different groups based on the identifying.

20. A non-transitory machine-readable storage medium, comprising executable instructions that, when executed by a processor, facilitate performance of operations, comprising:

facilitating rendering medical images of a liver of a patient in a graphical user interface of a medical imaging application that facilitates evaluating the medical images, wherein the facilitating comprises associating different groups of the medical images in different windows of the graphical user interface, the different groups corresponding to different hepatic vascular phases;

identifying an observation on the liver as depicted in at least some medical images;

determining, based on application of one or more feature detection algorithms to the at least some of the medical images, whether each feature included in a defined set of features is present or absent for the observation, wherein the one or more feature detection algorithms are configured to detect each feature in a subset of the different groups;

providing feature information via the graphical user interface indicating whether each feature is present or absent for the observation, and wherein the feature information comprises, for a feature being indicated as present, an interactive view button associated with the feature;

identifying a representative medical image of the at least some of the medical images comprising the feature; and rendering, in response to selection of the interactive view button, the representative medical image in a window of the different windows corresponding to a group of the different groups to which the representative image belongs.

21. The non-transitory machine-readable storage medium of claim 20, wherein the operations further comprise:

determining a hepatocellular carcinoma (HCC) classification score for the observation based on results of the one or more feature detection algorithms; and providing the HCC classification score via the graphical user interface.

* * * * *